(12) United States Patent
Vecerina et al.

(10) Patent No.: US 9,511,385 B2
(45) Date of Patent: Dec. 6, 2016

(54) AUTOMATED STENT COATING APPARATUS AND METHOD

(71) Applicant: Biosensors International Group, Ltd., Hamilton (BM)

(72) Inventors: Ivan Vecerina, Lausanne (CH); Vinh Pham, Rancho Santa Margarita, CA (US)

(73) Assignee: BIOSENSORS INTERNATIONAL GROUP, LTD., Hamilton (BM)

( * ) Notice: Subject to any disclaimer, the term of this patent is extended or adjusted under 35 U.S.C. 154(b) by 216 days.

(21) Appl. No.: 14/042,682

(22) Filed: Sep. 30, 2013

(65) Prior Publication Data

US 2014/0245952 A1 Sep. 4, 2014

Related U.S. Application Data

(63) Continuation of application No. 12/742,591, filed as application No. PCT/US2008/083700 on Nov. 14, 2008, now Pat. No. 8,573,150.

(Continued)

(51) Int. Cl.
*A61L 33/00* (2006.01)
*B05B 12/02* (2006.01)
(Continued)

(52) U.S. Cl.
CPC ................ *B05B 12/02* (2013.01); *A61L 31/00* (2013.01); *B05B 12/122* (2013.01); *B05B 12/126* (2013.01); *B05B 13/0235* (2013.01)

(58) Field of Classification Search
CPC ........... A61L 33/00; B05C 11/00; B05C 13/00
(Continued)

(56) References Cited

U.S. PATENT DOCUMENTS 4,614,300 A 9/1986 Falcoff
4,877,745 A 10/1989 Hayes et al.
(Continued)

FOREIGN PATENT DOCUMENTS

CN 1644184 A 7/2005
JP 2005-534399 A 11/2005
(Continued)

OTHER PUBLICATIONS

Biosensors Cardiology (BC) Conference, Aug. 3, 2005, presentation, 37 pages. http://ss1.shareinvestor.com/ir/biosensors/conference_20050803/3_john_shulze.asx.
(Continued)

*Primary Examiner* — Cachet Sellman
(74) *Attorney, Agent, or Firm* — Kilpatrick Townsend & Stockton LLP

(57) ABSTRACT

An automated apparatus and method for coating medical devices such as an intravascular stent, are disclosed in the method, a 2-D image of a stent is processed to determine (1) paths along the stent skeletal elements by which a stent secured to a rotating support element can be traversed by a dispenser head whose relative motion with respect to the support element is along the support-element axis, such that some or all of the stent skeletal elements will be traversed (2) the relative speeds of the dispenser head and support element as the dispenser head travels along the paths, and (3), and positions of the dispenser head with respect to a centerline of the stent elements as the dispenser head travels along such paths The rotational speed of the support and relative linear speed of the dispenser are controlled to achieve the desired coating thickness and coating coverage on the upper surfaces, and optionally, the side surfaces, of the stem elements.

18 Claims, 8 Drawing Sheets

Related U.S. Application Data

(60) Provisional application No. 60/987,963, filed on Nov. 14, 2007.

(51) Int. Cl.
*B05B 12/12* (2006.01)
*B05B 13/02* (2006.01)
*A61L 31/00* (2006.01)

(58) Field of Classification Search
USPC .................. 427/2.24; 118/663, 669; 356/27
See application file for complete search history.

(56) References Cited

U.S. PATENT DOCUMENTS

| | | | |
|---|---|---|---|
| 5,001,353 A | 3/1991 | Odake et al. | |
| 5,229,840 A | 7/1993 | Amarson et al. | |
| 5,429,682 A | 7/1995 | Harlow et al. | |
| 5,464,650 A | 11/1995 | Berg et al. | |
| 5,709,905 A | 1/1998 | Shaw et al. | |
| 5,757,498 A | 5/1998 | Klein et al. | |
| 5,837,313 A | 11/1998 | Ding et al. | |
| 5,873,904 A | 2/1999 | Ragheb et al. | |
| 6,001,311 A | 12/1999 | Brennan | |
| 6,096,070 A | 8/2000 | Ragheb et al. | |
| 6,121,027 A | 9/2000 | Clapper et al. | |
| 6,128,087 A | 10/2000 | Meredith, Jr. et al. | |
| 6,169,550 B1 | 1/2001 | Jain | |
| 6,209,621 B1 | 4/2001 | Treacy | |
| 6,214,407 B1 | 4/2001 | Laube et al. | |
| 6,321,591 B1 | 11/2001 | Breunsbach et al. | |
| 6,395,326 B1 | 5/2002 | Castro et al. | |
| 6,572,644 B1 | 6/2003 | Mocin | |
| 6,616,765 B1 | 9/2003 | Castro et al. | |
| 6,645,547 B1 | 11/2003 | Shekalim et al. | |
| 6,778,694 B1 | 8/2004 | Alexandre | |
| 6,836,700 B2 | 12/2004 | Greene et al. | |
| 6,939,376 B2 | 9/2005 | Shulze et al. | |
| 6,997,992 B2 | 2/2006 | Nesbitt | |
| 7,048,962 B2 | 5/2006 | Shekalim et al. | |
| 7,101,508 B2 | 9/2006 | Thompson et al. | |
| 7,125,577 B2 | 10/2006 | Chappa | |
| 7,220,755 B2 * | 5/2007 | Betts | C07D 498/18 514/291 |
| 7,232,490 B1 | 6/2007 | Hossainy | |
| 7,258,891 B2 | 8/2007 | Pacetti et al. | |
| 7,405,813 B2 | 7/2008 | Park | |
| 7,416,609 B1 | 8/2008 | Madriaga et al. | |
| 7,455,876 B2 | 11/2008 | Castro et al. | |
| 7,478,008 B2 | 1/2009 | Balss et al. | |
| 7,485,333 B2 | 2/2009 | Pacetti et al. | |
| 7,485,335 B2 | 2/2009 | Villareal et al. | |
| 7,569,110 B2 | 8/2009 | Shekalim et al. | |
| 7,628,859 B1 | 12/2009 | Hossainy et al. | |
| 7,654,775 B2 | 2/2010 | Ruckman | |
| 7,704,544 B2 | 4/2010 | Pacetti et al. | |
| 7,718,213 B1 | 5/2010 | Scheer | |
| 7,879,386 B2 | 2/2011 | Pacetti et al. | |
| 7,892,592 B1 | 2/2011 | Chen et al. | |
| 7,976,891 B1 | 7/2011 | Van Sciver et al. | |
| 8,104,427 B2 | 1/2012 | Shekalim et al. | |
| 8,134,700 B2 | 3/2012 | Cameron et al. | |
| 8,573,150 B2 | 11/2013 | Vecerina et al. | |
| 2002/0085054 A1 | 7/2002 | Tokie | |
| 2003/0003220 A1 | 1/2003 | Zhong et al. | |
| 2003/0207019 A1 * | 11/2003 | Shekalim | B05B 12/12 427/2.24 |
| 2003/0207022 A1 | 11/2003 | Shekalim et al. | |
| 2004/0110439 A1 | 6/2004 | Chaikof et al. | |
| 2004/0185081 A1 | 9/2004 | Verlee et al. | |
| 2004/0202773 A1 | 10/2004 | Verlee et al. | |
| 2004/0211362 A1 | 10/2004 | Castro et al. | |
| 2004/0218798 A1 | 11/2004 | Abdel-Fattah et al. | |
| 2005/0266039 A1 | 12/2005 | Weber | |
| 2006/0099649 A1 | 5/2006 | Goh et al. | |
| 2006/0202369 A1 | 9/2006 | Foreman et al. | |
| 2007/0139541 A1 * | 6/2007 | Fein | G01N 21/6458 348/294 |
| 2007/0191936 A1 | 8/2007 | Williams et al. | |
| 2008/0094428 A1 | 4/2008 | Otis et al. | |
| 2008/0226812 A1 | 9/2008 | Chen | |
| 2008/0286440 A1 | 11/2008 | Scheer | |
| 2009/0074943 A1 | 3/2009 | Fredrickson et al. | |
| 2009/0226601 A1 | 9/2009 | Zhong et al. | |
| 2009/0288597 A1 | 11/2009 | Shekalim et al. | |
| 2009/0291196 A1 | 11/2009 | Morris et al. | |
| 2010/0003396 A1 | 1/2010 | Verlee et al. | |
| 2010/0034960 A1 | 2/2010 | Kindaichi et al. | |
| 2010/0053317 A1 | 3/2010 | Freifeld et al. | |
| 2010/0183799 A1 | 7/2010 | Sciver et al. | |
| 2010/0262230 A1 | 10/2010 | Vecerina et al. | |
| 2011/0239939 A1 | 10/2011 | Van Sciver et al. | |
| 2011/0271904 A1 | 11/2011 | Van Sciver | |
| 2013/0090879 A1 | 4/2013 | Estor et al. | |
| 2013/0206741 A1 | 8/2013 | Pfeifer et al. | |

FOREIGN PATENT DOCUMENTS

| | | |
|---|---|---|
| JP | 2005-534946 A | 11/2005 |
| JP | 2006-505359 A | 2/2006 |
| KR | 10-2004-0016721 A | 2/2004 |
| WO | 2004/043300 A1 | 5/2004 |
| WO | 2006/048243 A1 | 5/2006 |
| WO | 2007/031854 A2 | 3/2007 |
| WO | 2008/114585 A1 | 9/2008 |

OTHER PUBLICATIONS

Biosensors International, Power point presentation given on Sep. 26, 2005 at the UBS Global Life Sciences Conference, New York City, Slides 1, 14 and 15 only.

Video ("Computer-Controlled Drug Application Video") as displayed in a display booth at (Oct. 17-21, 2005), at the Transcatheter Cardiovascular Therapeutics Conference, in Wash., D.C.

* cited by examiner

AUTOMATED STENT COATING APPARATUS AND METHOD

CROSS-REFERENCES TO RELATED APPLICATIONS

This application is a continuation of U.S. patent application Ser. No. 12/742,591, filed Jun. 23, 2010, (now U.S. Pat. No. 8,573,150, issued Nov. 5, 2013) which is the National Stage of International Application No. PCT/US2008/083700, filed Nov. 14, 2008, which claims the benefit of U.S. Provisional Application 60/987,963, filed Nov. 14, 2007, the disclosures of which are incorporated herein by reference.

TECHNICAL FIELD

The present application relates to apparatus for coating medical devices, such as endovascular stents, and an automated coating method.

BACKGROUND

Vascular occlusion or atherosclerosis of coronary arteries is commonly treated by a procedure known as percutaneous transluminal coronary angioplasty (PTCA), in which the occluded artery is expanded by a balloon secured at the distal end of a catheter, and retained in its expanded condition by a radially expandable stent secured to the balloon and implanted at the site of occlusion.

Complications that can arise from stent therapy include restenosis and thrombosis. In an effort to overcome these complications, stents may contain a layer or coating of an anti-restenosis drug that is released in a controlled fashion at the stent-implantation site. Typically, the drug is contained in a permanent or bioerodable polymer carrier, as disclosed, for example, in U.S. Pat. No. 5,716,981 issued to Hunter et al. entitled "Anti-angiogenic Compositions and Methods of Use." Examples of drugs that can be delivered in this manner are antiproliferatives, anticoagulants, anti-inflammatory agents and immunosuppressive agents. The polymer carrier with drug may be covered by a porous biodegradable layer that serves to regulate controlled release of the drug into the body, as disclosed for example, in U.S. Pat. Nos. 6,774,278 and 6,730,064.

A variety of methods have been employed for coating implantable medical devices, such as stents, with a biological active agent. Soaking or dipping the implantable device in a bath of liquid medication is taught in U.S. Pat. No. 5,922,393 to Jayaraman and U.S. Pat. No. 6,129,658 to Delfino et al. Devices introducing heat and/or ultrasonic energy in conjunction with the medicated bath are disclosed in U.S. Pat. No. 5,891,507 to Jayaraman and U.S. Pat. No. 6,245,104 B1 to Alt. U.S. Pat. No. 6,214,115 B1 to Taylor et al. discloses spraying the medication through pressurized nozzles.

The coating methods noted above result in a coating that covers both outer and inner surfaces of the stent. This may lead to unwanted drug- or polymer-related effects at the interior surface of the stent (the surface exposed to blood flow within the stented vessel), or the coating may crack or break away when the implantable device is removed from the implantation apparatus, e.g., after balloon expansion and removal of the catheter balloon, with potentially catastrophic blood clotting effects.

For purposes of coating the outer surface of a stent only, various methods employing ink-jet deposition procedures have been proposed. In the paper "Applications of Ink-Jet Printing Technology to BioMEMS and Microfluidic Systems," presented at the SPIE Conference on Microfluidics and BioMEMS, October 2001, the authors, Patrick Cooley, David Wallace, and Bogdan Antohe provide a fairly detailed description of Ink-Jet technology and the range of its medically related applications. A related device is disclosed in U.S. Pat. No. 6,001,311 to Brennan, which uses a moveable two-dimensional array of nozzles to deposit a plurality of different liquid reagents into receiving chambers. In the presentation of Cooley and the device of Brennan, the selective application of the material is based on an objective predetermined location of deposit rather that on a subjective placement as needed to meet the requirements of a specific application procedure. Yet another approach is disclosed in U.S. Pat. No. 6,645,547 to Shekalim, et al. which utilizes a drop-on-demand inkjet print head to selectively coat a stent, while avoiding a balloon.

Another coating method, namely micropipetting, has also been proposed. However, micropipetting may result in certain coating imperfections. For example, an imperfection known as bridging, and indicated at 102 in FIG. 7, occurs when material being applied to the crown of a stent band enters in contact with a band to a crown in an adjacent band, forming a stable bridge across the two bands. This type of anomaly is unacceptable because the bridge coating material is likely to break free of the stent on stent expansion when deployed, creating a potentially dangerous foreign object in the blood stream.

Another imperfection is a meniscus, such as shown at 104 and 106, formed across opposite side regions of a crown. Because of superficial tension, when going around a crown, a droplet tends to be stretched across the crown, and to create a meniscus within the crown. Such a meniscus may break into pieces during stent expansion, and fragments may be liberated. In general, this type of imperfection is acceptable if the area of the meniscus is small, for example if it does not exceed ⅓ of the total area of the crown region, defined as the area between dimension markers 108. This, meniscus 104 in the figure would be considered acceptable, while meniscus 106 would be considered unacceptable.

Another coating anomaly, coating overhang, refers to the coating material that extends beyond the edges of the stent element outer surfaces, such as shown at 110 in FIG. 7. In some cases, and as described further below, it is desirable to position a dispensing head for coating overflow from the outer to the side surfaces, such that coating is applied to both the upper and side surfaces of the stent elements. For this type of coating, it is necessary to achieve coating overhang. However, it is important in this process that the overhanging coating portions from adjacent struts do not fuse to form an overhang that bridges the two struts, as illustrated at 112 in FIG. 7.

Yet another type of imperfection is coating that extends to the inner surface of stent elements, as indicated at 114 in FIG. 7. This type of imperfection can occur by excessive coating applied to the outer surface of a stent element, particularly if applied near an edge region of the element, resulting in coating material flowing down the side and onto the inner surface of the element. This type of imperfection may be dangerous in that the overhanging coating can break away from the stent's inner surface, particularly on stent expansion at the site of vascular injury.

The algorithms of the present invention described below are designed to minimize such coating imperfections, while achieving a uniform coating of the stent elements, and in one embodiment, to achieve a stent coating in which coating is applied to both outer and side surfaces of the stent in a selected ratio of material, e.g., where the side coating is 50%-100% of the amount applied to the outer surfaces of the stent elements.

Ideally, a method of coating a medical device, such as a stent, with a drug-containing coating would produce an overall precise amount of drug in the coating and a substantially uniform coating over the outer surfaces of the stent elements. At the same time, in order to reduce the thickness of the coating on the outer surface of the stent elements, and the resistance of the coating to cracking during stent expansion, it may be desirable to apply some portion of the coating, e.g., 10% to 60% of the total coating amount, to side regions of the stent elements, where the coating would still be accessible to the surrounding tissue.

SUMMARY OF THE INVENTION

The invention includes, in one aspect, an apparatus for creating a coating on the outer surface of a stent whose tubular structure is composed of linked skeletal elements. The apparatus includes:

(a) a support element adapted to support such a stent during a coating operation;

(b) a dispenser having a dispensing head through which coating material can be applied in liquid form, at a selected rate, as the dispensing head moves relative to the support element, (c) first and second electromechanical devices for (i) synchronously rotating the support element at a selected rotational speed, and (ii) translating the dispensing head relative to the support element in a direction along said support element axis, respectively, (d) an imaging system adapted to capture a representation of such a stent, and (e) a control unit operatively connected to the imaging system and to the first and the second electromechanical devices for:

(e1) processing the representation of the stent obtained with the imaging system to determine (i) paths along the stent skeletal elements by which a stent secured to the support can be traversed by the dispenser head, in one or more passes, such that some or all of the stent skeletal elements will be traversed, (ii) the relative speeds of the support element and dispenser head as said paths are traversed, and (iii) positions of the dispenser head with respect to a centerline of the stent elements, as the paths are traversed, and (e2) synchronously activating the first and second electromechanical devices in order to move the dispensing head relative to support element along the paths and with the relative speeds and positions determined in (e1).

Where the apparatus is used in producing on the stent, a coating containing a preselected amount of a therapeutic compound, the processing step (e1) may further include determining the paths and relative speeds needed to deposit on the stent, a total amount of coating material containing the preselected amount of the therapeutic drug.

The apparatus may include a third electromechanical device operatively connected to the dispenser and control unit, and the control unit may be operable to adjust the rate of material dispensed from the dispenser head, as the dispenser head travels along said paths.

The apparatus may include a fourth electromechanical device operatively connected to the control unit and dispenser, and the control unit may be operable to move the dispenser toward and away from the support fixture, to place the dispensing head a selected distance from the outer surface of a stent secured to the support, as the dispenser head travels along said paths.

The imaging system in the apparatus may be operable to distinguish the outer surface of the stent secured to the support fixture, as the support fixture is axially rotated or translated, to construct a two-dimensional representation of the stent skeletal elements.

The control unit, in carrying out step (e1), may be operable to apply (i) a segmentation algorithm to determine the areas in the representation that are occupied by the stent elements, a (ii) skeletonization algorithm, to determine a curve along the medial axis of the stent skeletal elements as well as their points of intersection with other stent skeletal elements, (iii) a path-traversal algorithm to determine the paths along the skeletal elements, and (iv) a speed and position algorithm to determine the relative speeds and positions of the dispenser head as it travels along said paths.

For use in applying a coating to the outer surface of a tubular stent having cylindrical band elements joined by axial links, the path-traversal algorithm applied by the control unit in step (e1) may be operable to determine paths by which the stent skeletal elements can be traversed by the dispenser head, in a selected number of passes, such that the stent skeletal elements will be traversed at least once, and link and band elements of the stent may traversed by different numbers of passes.

The path-traversal algorithm applied by the control unit in step (e1) may be operable to determine the total length of the determined path and the volume to be dispensed, and said speed and position algorithms are determined so that the preselected amount of coating material is applied.

For use in applying a coating to the outer surface of a tubular stent having substantially straight strut skeletal elements with widths greater than the width of the dispenser head, the speed and position algorithm applied by the control unit in step (e1) may be operable to determine the positions of the dispensing head, relative to the width centerline of such struts, for different passes, such that coating is applied across the entire width of the struts in the course of several passes.

The speed and position algorithm applied in (e1) may be further operable to determine relative speed and positions of the dispenser head needed to produce coating material spillover onto the side surfaces of the stent elements, in a desired amount typically between 10%-60% of the amount of coating material applied to the upper stent element surfaces.

For use in applying a coating to the outer surface of a tubular stent having curved (rounded or angled) crown skeletal elements, the speed and position algorithm applied by the control unit in step (e1) may be operable to determine the positions of the dispensing head relative to the width centerline of a curved element, and to control the relative speed of movement of the dispensing head, so as to minimize the potential for material-coat bridging between laterally-adjacent crown elements and meniscus formation across the inner edge region of a crown element.

For use in applying a coating to the outer surface of a tubular stent having substantially straight strut skeletal elements connected by substantially curved crown elements, the speed and position algorithm applied by the control unit in step (e1) is applied to determine a relative dispenser-head speed that is dependent on the local curvature of the trajectory. Alternatively, the algorithm may determine a constant speed.

For use in applying a coating to the outer surface of a tubular stent also having connecting link elements, the speed and position algorithm performed by the control unit in step (e1) is operable to determine independent dispenser speeds for the link elements.

In another aspect, the invention includes an automated method of applying a coating to the outer surface of a stent whose tubular structure is composed of linked skeletal elements. The method includes the steps of:

(a) processing an image of such a stent to determine (a1) paths along the stent skeletal elements by which a stent secured to a support element that can be axially rotated and translated relative to a dispenser head, such that some or all of the stent skeletal elements will be traversed, (a2) the relative speeds of the dispensing head and support element as said paths are traversed, and (a3), and positions of the dispenser head with respect to a centerline of the stent elements, as said paths are traversed, and (b) synchronously activating a first electromechanical device that controls the rotational motion of the support element and a second electromechanical device that controls the relative linear motion of the dispensing head with respect to the support element along the support element axis, in order to move the dispensing head relative to the support element along the paths and with the relative speeds and positions determined in step (a).

Step (a1) in the method may include the steps of applying (i) a segmentation algorithm to determine the area occupied by the stent elements, a (ii) sketetonization algorithm, to determine the points of intersections of the stent skeletal elements, (iii) a path-traversal algorithm to determine the paths along the skeletal elements, and (iv) a speed and position algorithm to determine the relative speeds and positions of the dispenser head as it travels along said paths.

Applying the path-traversal algorithm may be operable to determine paths by which the stent skeletal elements can be traversed by the dispenser head, in a selected number of passes over given portions of the skeletal elements, such that all the stent skeletal elements will be traversed at least once, and link and band elements of the stent may traversed by different numbers of passes.

The path-traversal algorithm may be operable to determine the total length of the determined path and the volume to be dispensed, and the speed and position algorithms are determined so that the preselected amount of coating material is applied.

For use in applying such a coating to the outer surface of a tubular stent having substantially straight strut skeletal elements with widths greater than the width of the dispenser head, the speed and position algorithm may be operable to determine the positions of the dispensing head, relative to the width centerline of such struts, for different passes, such that coating is applied across the entire width of the struts in the course of several passes.

For use in applying such a coating to the outer and side surfaces of the stent element, the speed and position algorithm applied in (e1) may be further operable to determine relative speed and positions of the dispenser head needed to produce coating material spillover onto the side surfaces of the stent elements, in a desired amount, typically between 10%-60% of the total amount of coating material applied to all the stent element surfaces.

For use in applying such a coating to the outer surface of a tubular stent having curved (rounded or angled) crown skeletal elements, the speed and position algorithm may be operable to determine the positions of the dispensing head relative to the width centerline of a crown element, and to control the relative speed of movement of the dispensing head, so as to minimize the potential for material-coat bridging between laterally-adjacent curved elements and meniscus formation across the inner edge region of a crown element.

For use for use in applying such a coating to the outer surface of a tubular stent having substantially straight strut skeletal elements connected by substantially rounded crown elements, the speed and position algorithm may be operable to determine a dispenser-head speed that is dependent on the local curvature of the trajectory. Alternatively, the algorithm may determine a constant speed.

For use in applying such a coating to the outer surface of a tubular stent also having connecting link elements, the speed and position algorithm may be operable to determine independent dispenser speeds for the link elements.

Also disclosed is computer-readable code which is operable, when used to control an electronic computer, to carry out the above method.

In still another aspect, the invention includes a coated, endovascular stent comprising a tubular structure composed of linked skeletal elements having outer, side and inner surfaces, and a selected amount of coating covering the upper and side surfaces of the stent elements, where the volume of coating covering the side surfaces of the elements is a selected amount in the range between 5-80%, preferably 10%-60% of the total amount covering all the surfaces of the elements.

These and other aspects and embodiments of the present invention will become better apparent in view of the detailed description in conjunction with the accompanying drawings.

DETAILED DESCRIPTION OF THE INVENTION

I. Definitions

Figure 1:
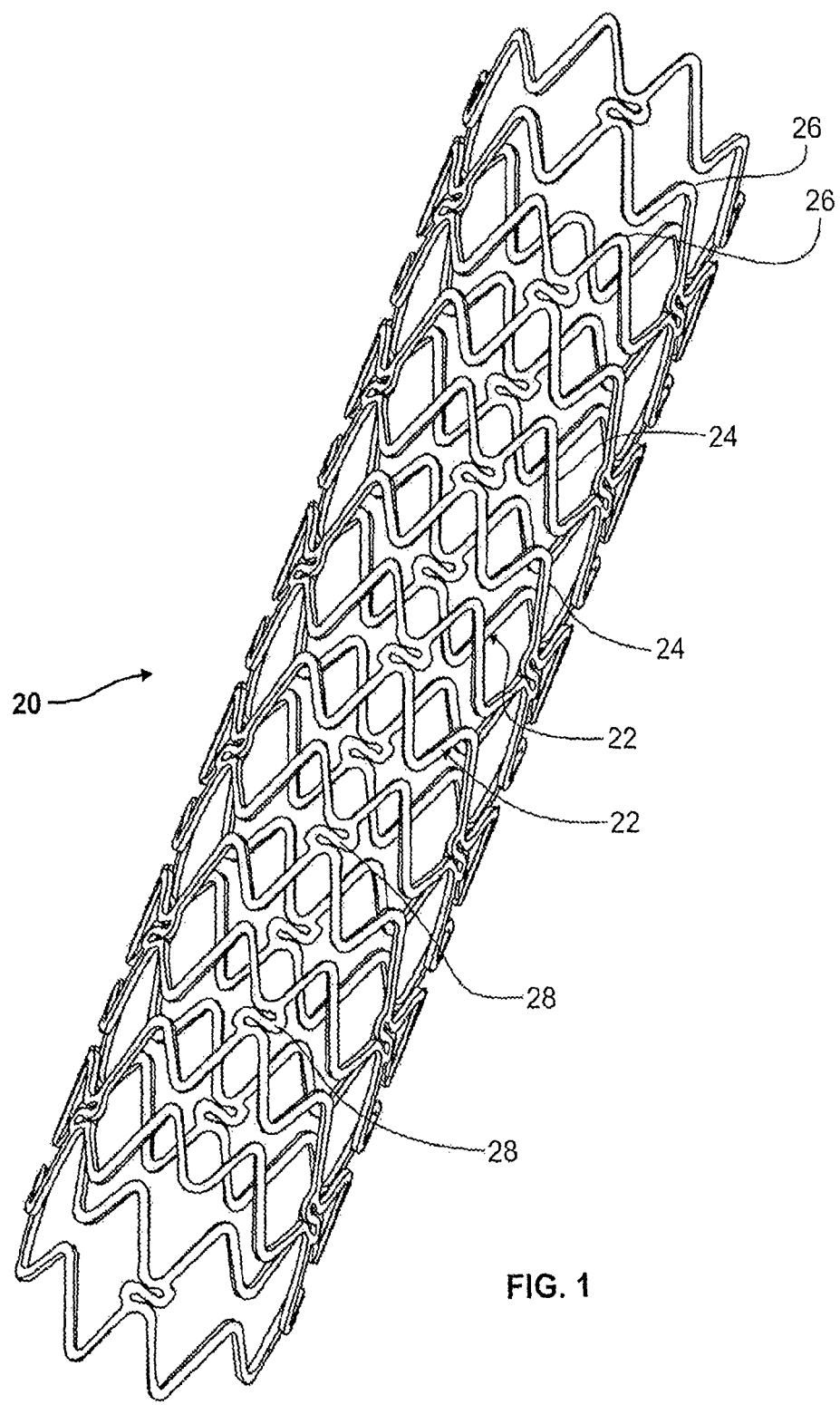
FIG. 1 is a perspective view of a tubular stent composed of linked skeletal elements.

Unless indicated otherwise, the following terms are accorded the following meanings.

A "coating of the outer surface of a stent," where the stent is composed of linked skeletal elements, refers to a coating that covers the outer (outwardly facing) surfaces of the stent elements, and optionally, also side surface, meaning the surfaces of the elements between the outer and inner (inwardly facing) surfaces of the stent elements. The coating may be a polymer without drug, a polymer containing a drug in releasable form, e.g., by polymer breakdown or drug diffusion from a polymer carrier, or a polymer-free drug-containing coating, such as a pure-drug coating or drug containing binders and/or excipients, such as phospholipids. In all cases, the coating can be applied in a liquid form, typically in liquid having a viscosity between 1-2000 centipoise and the coating, once applied, can dry or cool to form a solid coating that is retained on the stent during stent placement at a vascular site.

A dispenser head "moving relative to a support element" means that one or both of the dispenser head and support element are moved relative to the other. Typically, the support element rotates and moves linearly with respect to a stationary dispenser head; alternatively, for example, the support element may rotate at a fixed linear position, and the dispenser head may move linearly along the axis of the rotating support element.

Likewise, a dispensing head "traversing a path along the elements of a stent" means that the dispensing head is moved relative to a stent secured to a support element, either by a combined rotation and linear movement of the support element relative to a stationary dispensing head or, for example, rotation of the support element and linear movement of the dispensing head along the support-element axis.

A "support element" is any structure capable of supporting a stent for rotation about a fixed axis. One preferred support element is a mandrel dimensioned to receive a stent securely thereon, for rotation with the mandrel about the mandrel's long axis.

"Limus drug" refers to macrocyclic triene immunosuppressive compound having the general structure shown, for example, in U.S. Pat. Nos. 4,650,803, 5,288,711, 5,516,781, 5,665,772 and 6,153,252, in PCT Publication No. WO 97/35575, in U.S. Pat. No. 6,273,913B1, and in U.S. Patent Application Nos. 60/176,086, 2000/021217A1, and 2001/002935A1.

"42-O-alkoxyalkyl limus drug" refers to the 42-O alkoxyalkyl derivative of rapamycin described in U.S. patent application 20050101624, published May 12, 2005, which is incorporated herein in its entirety. As exemplary "42-O-alkoxyalkyl limus drug" is "42-O-ethoxyethyl rapamycin".

"Polymer-free coating" means a coating whose structure and cohesiveness are provided by the drug itself, with or without the presence of one or more binding agents, rather than by a polymer matrix in which the drug is embedded, i.e., a polymer carrier.

II. Apparatus and Method

A. Intravascular Stent

FIG. 1 illustrates one embodiment of a stent 20 in accordance with the present invention, in a contracted state. The stent is typically formed by laser cutting a metal or polymer tube having inner and outer diameters of about 1.7 and 2.0 mm, respectively, and tube lengths typically between about 8-50 mm. As seen, the stent is composed of linked skeletal elements, which include a plurality of circumferential bands, such as bands 22, each having a sinusoidal or rounded-tip sawtooth pattern made up of substantially straight struts or strut elements, such as struts 24, connected by curved crowns or crown elements, such as crowns 26. As will be seen below with respect to FIGS. 9 and 10, the struts 118 have a relatively greater width dimension, typically on the order of 0.12 to 016 mm over the major portion of the strut length, and taper at their end regions to a reduced width of between about 0.07 to 0.10 mm to match the width dimension of the crowns 120 in each band. Although the curved crowns in the stent shown are rounded, the curved crowns may also be sharply angled, where the bands making up the stent comprise a sawtooth pattern.

Figure 5A:
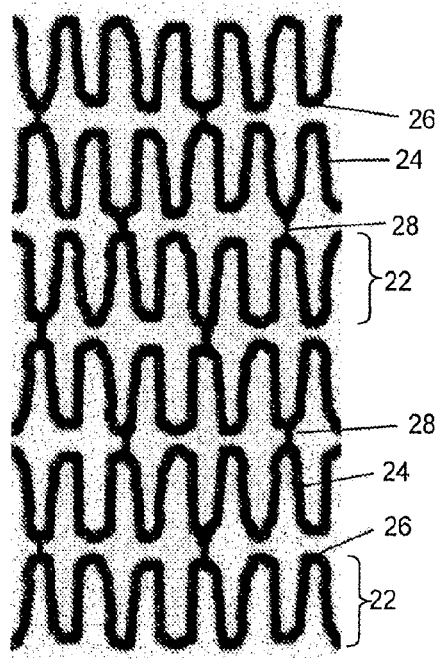
FIGS. 5A and 5B show a grayscale image of a stent in 2-D representation (5A) and a binary image of the same stent (5B), respectively.
Figure 5B:
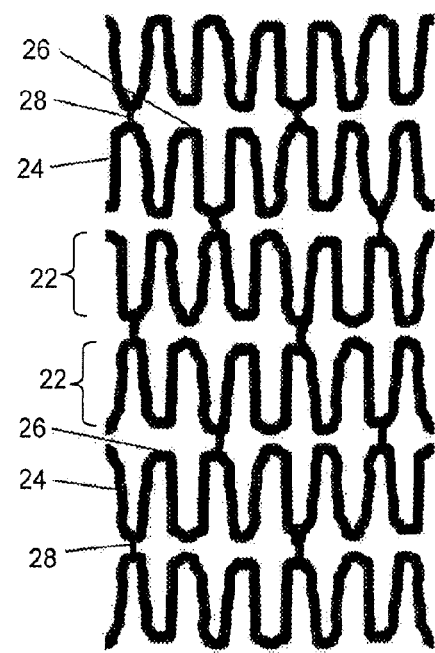
Figures 9A, 9B:
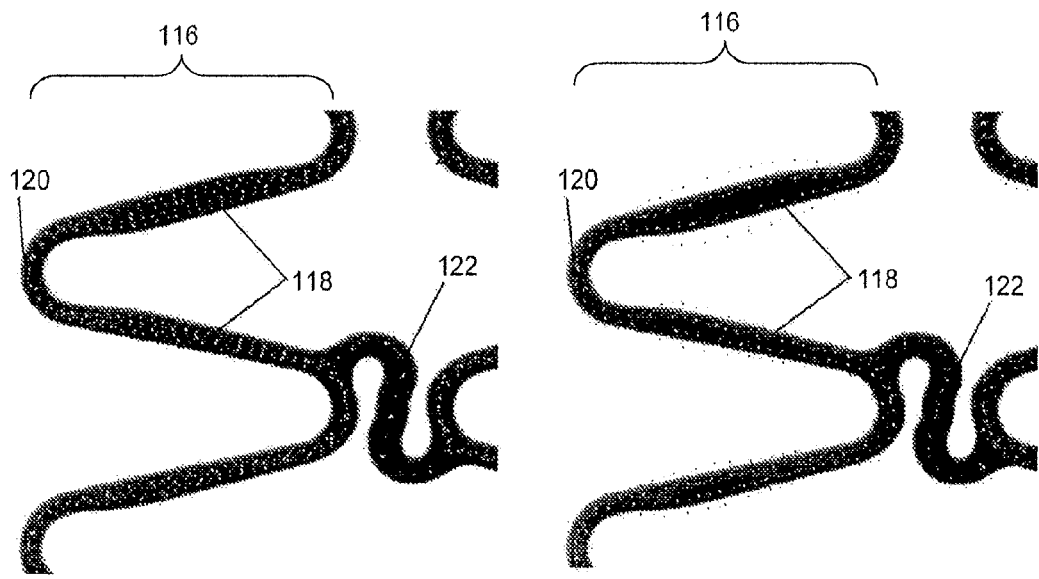
FIGS. 9A and 9B shows paths (dotted lines) with an R-spread margin of 30 microns, a multiplier of 1 (9A) or 3 (9B), each with 4 distinct trajectories.
Figure 10:
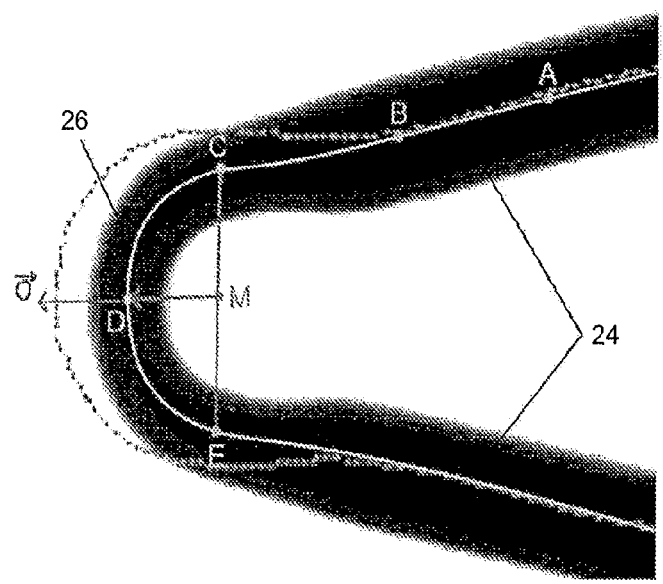
FIG. 10 shows parameters for analyzing path contours in the crown or any other curved region of a stent.

Referring back to FIG. 1, the bands 22 in the stent 20 are connected one to another by links 28 joining the crown regions of adjacent bands to one another. In the embodiment shown in FIGS. 5A and 5B, every third crown 26 in a band 22 is linked to a confronting crown in an adjacent band, and the links are offset, from band to band, to distribute the links relatively evenly along the length of the stent. The links 28 connecting adjacent stent bands 22 may be substantially straight links 28, as shown in FIGS. 5A, 5B and 6, or may be curved links 122, as shown in FIGS. 9A and 9B. It will be appreciated that the stent construction allows both radial expansion, primarily accommodated by bending in the crowns to allow expansion in each band, and bending along the stent's long axis, accommodated by combined outer expansion and inner compression within the bands and by uneven expansion of links in the direction of bending.

In one embodiment of the invention, the stent is designed for delivery in a contracted state over a catheter balloon, and is deployed at a site of vascular injury by balloon expansion, causing the stent to expand radially so that the outer surfaces of the stent are pressed against the vascular wall, to anchor the stent in place. The contracted-state diameter of the stent is between approximately 0.5 mm-2.0 mm, preferably 0.71 to 1.65 mm, and a length of between 5-100 mm, preferably 8-50 mm. The expanded stent diameter may be a multiple of the contracted stent diameter. For example, a stent with a contracted diameter of between 0.7 to 1.7 mm may expand radially to a selected expanded state of between 2.0 and 4.0 mm or more. Stents having this general stent-body architecture of linked, expandable tubular members are known, for example, as described in PCT Publication No. WO 99/07308, which is commonly owned and expressly incorporated by reference herein.

Preferably, the stent structure is made of a biocompatible material, such as stainless steel. Further examples of biocompatible materials that may also be used are cobalt chromium, nickel, magnesium, tantalum, titanium, nitinol, gold, platinum, inconel, iridium, silver, tungsten, other biocompatible metals, or alloys thereof, carbon or carbon fiber, cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or other biocompatible polymeric materials, or mixtures or copolymers thereof, poly-L-lactic acid, poly-DL-lactic acid, polyglycolic acid or copolymers thereof, polyanhydride, polycaprolactone, polyhydroxybutyrate valerate or another biodegradable polymers, or mixtures or copolymers thereof, protein, extracellular matrix components, collagen, fibrin or other biologic agents, or a suitable mixture thereof. An example of a typical stent is described in U.S. Pat. No. 6,730,064.

B. Coating Apparatus

Figure 2:
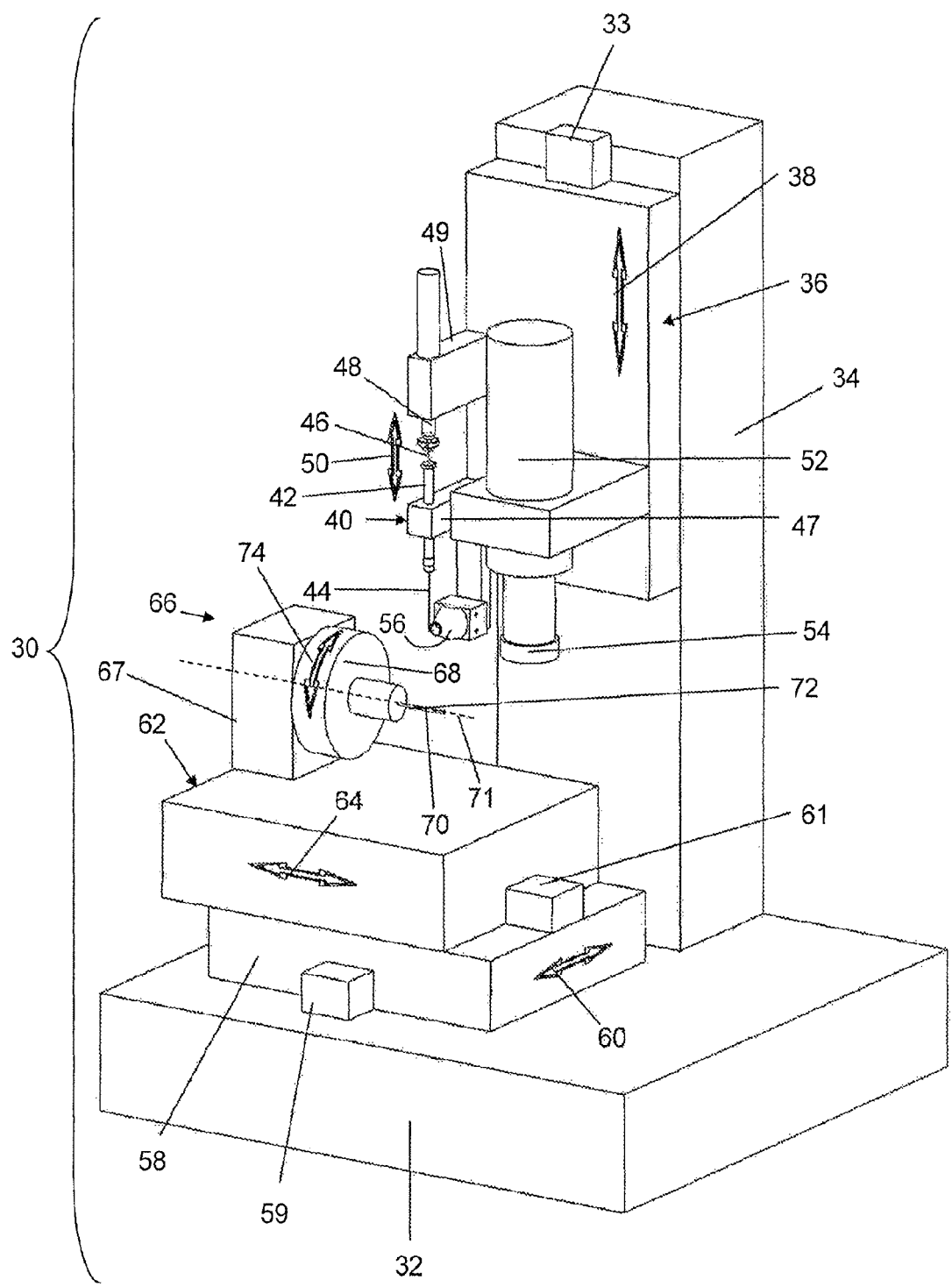
FIG. 2 is a perspective view of the apparatus of the invention.
Figure 3A:
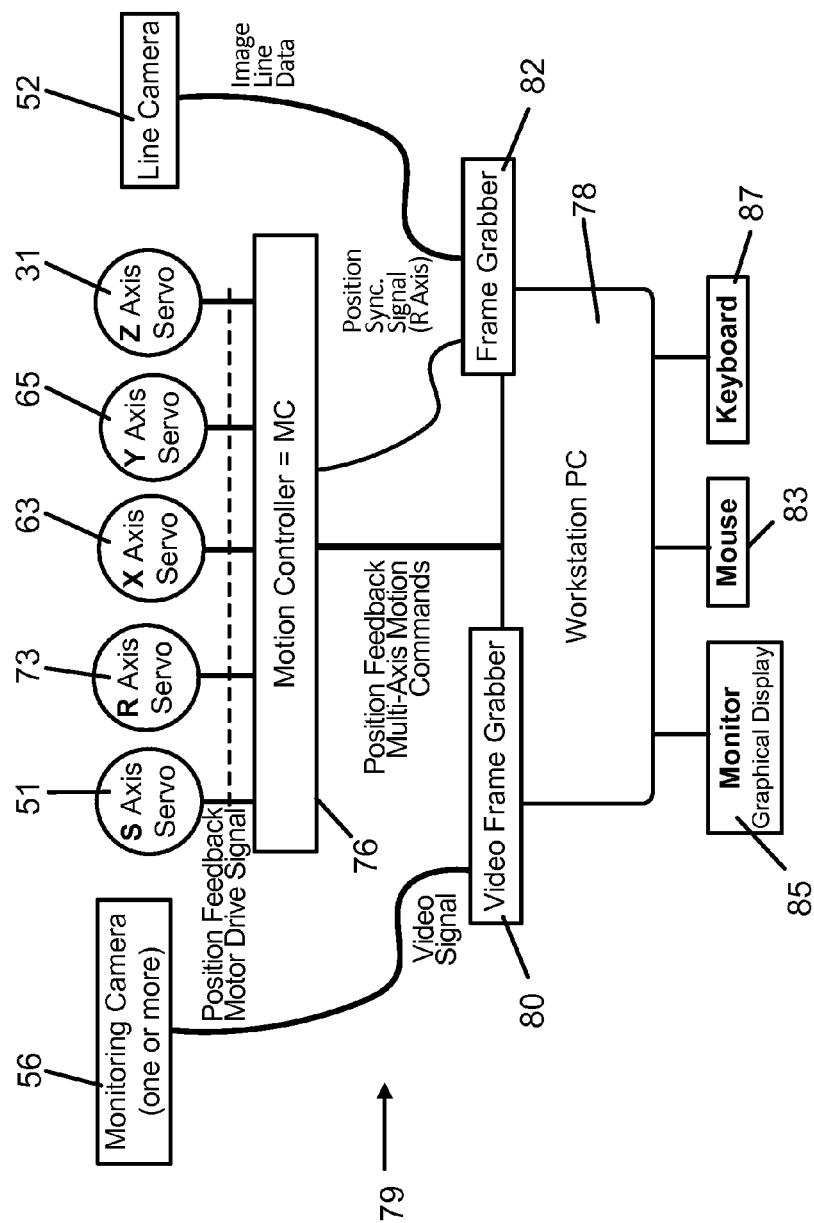
FIGS. 3A and 3B are block diagrams illustrating a portion of the interactive connections among some of the mechanical and control components of the apparatus of the invention (3A), and control unit operations in controlling the apparatus (3B), respectively.

FIG. 2 shows an apparatus 30 constructed in accordance with one embodiment of the invention. The apparatus generally includes a base 32 supporting a vertical column 34. Mounted on vertical column or support 34 is a vertical stage support 33 on which a Z-axis stage (i.e., vertical motion stage) 36 is slidably mounted, e.g., by rollers or bearings, for movement in a vertical (Z-axis) direction, indicated schematically by double arrow 38, under the control an electromechanical motor. One exemplary motor is a MCG IB17001 servo motor, available from MCG USA (Prior Lake, Minn.), coupled with the stage using a driving screw (not shown). Feedback on the actual motion is provided by a high resolution encoder (not shown), such as a RGH22H30D62 encoder head, attached to the stage 36 (or other suitable surface) reading an A-9523-6030 encoder scale (not shown) attached to the column 34, both available from Renishaw (Chicago, Ill.), providing a resolution of 0.05 microns, typically over a total translation distance of about 20 cm. As shown in FIG. 3A, the motor 31, which is also referred to herein as an electromechanical device, is controlled by a motion controller 76 in a control unit 79, as described below with respect to FIG. 3A. Alternatively, referring back to FIG. 2, the Z-axis stage may be slidably mounted on base 32 to an adjustable height, and retained there by a conventional tightening clamp or the like (not shown).

Mounted on the Z-axis stage is a dispenser assembly 40 which functions to hold a syringe 42, and to control the dispensing rate of liquid from the syringe during a coating operation. The syringe includes a needle 44, from which coating material is dispensed, and a plunger 46, which is depressed into the syringe to dispense material from the syringe. The syringe is mounted on the Z-axis stage, for vertical motion therewith, by a mounting bracket 47. A syringe model employed determines the µl/mm "pitch" of the dispensing, that is, the microliters of solution dispensed for each millimeter by which the syringe plunger is advanced. One group of exemplary models includes Hamilton 1700 Series Gastight syringes from 10 µl to 500 µl, whose graduations are spread over a range of 60 mm. Exemplary needles include conventional conical- or blunt-end needles having a selected needle gauge of between 22 and 30, preferably about 26. The syringe needle, particularly the tip of the syringe needle, is also referred to herein as a dispensing head.

Movement of the plunger, which controls the rate of dispensing from the syringe, is under the control of a dispensing rod 48 mounted on the Z-axis stage, for Z-axis movement therewith, by a mounting bracket 49 attached to the stage. Rod 48 is also independently movable within bracket 49, in a Z-axis direction, to control the downward motion of the plunger in the syringe, thereby to control the dispensing rate of coating material from the syringe. Movement of the dispenser rod, indicated schematically by double arrow 50, is under the control of an electromechanical motor (not show). One exemplary motor is a high-resolution PI M-227.50 "mike" motor (PI/Physik Instrumente, Auburn, Mass.), with a non-rotating tip driven by a closed-loop DC motor supporting a minimum incremental motion of 0.05 µm. This motor is rigidly mounted above a syringe holder 40, and directly pushes onto the plunger 46 of the syringe. An interfacing element (not shown) on the dispensing rod 48 holds the plunger of the syringe in a stable and centered fashion. As seen in FIG. 3A, the dispensing unit motor 51 is controlled by motion controller 76, allowing full synchronization of the dispensing with the positioning of the dispensing unit over the stent. Like the motor 31 that controls the vertical motion 38, motor 51 is also referred to herein as an electromechanical device and is controlled by a motion controller 76 in a control unit 79, as described below.

Referring back to FIG. 2, the Z-axis stage 36 also includes an imaging system comprising a line camera 52, including one or more optical lenses 54, for producing a grayscale image of a stent and a monitoring camera 56, for monitoring the coating process during operation of the apparatus, as will be further discussed below. The monitoring camera 56 is adjustably mounted on stage 36 for viewing the tip of the syringe needle and portion of the stent to which coating is being applied during a coating operation, as will be described below with respect to FIG. 11.

As seen in FIG. 3A, the control unit 79 of the present invention comprises line camera 52, monitoring camera 56, motion controller 76 and workstation 78. Line camera 52 is operatively connected to control unit 79 via a frame grabber 82. Similarly, monitoring camera 56 is operatively connected to the control unit 79 via a frame grabber 80.

One exemplary line camera is the P2-23-06K40 available from DALSA (Colorado Springs, Colo.), which provides a resolution of 6144 pixels on a single line. In one embodiment of the invention, the workstation 78 comprises a Windows-based PC, which is powerful enough to process large scanned images provided on the system, with at least 2 Gigabytes of memory and two processing cores.

Referring back to FIG. 2, the apparatus 30 includes a Y-motion stage 58 that is slidably mounted, e.g., by rollers or bearings, on a base-mounted support 59 for movement in a horizontal-plane Y direction, indicated schematically by the double-line arrow 60, under the control an electromechanical motor (not shown). One exemplary motor is a BLMUC-143 linear forcer acting within a BLTUC-416 magnetic track, both available from Aerotech (Pittsburgh, Pa.). Position and motion measurements are recorded with a resolution of 0.05 microns, using the same encoders as for the Z axis, available from Renishaw. The total translation distance is of about 20 cm. As illustrated in FIG. 3A, the motor 65 is controlled by a motion controller 76 in control unit 79. In an alternate embodiment, the Y-motion stage 58 may be slidably mounted on the base to an adjustable Y-axis position, and retained there by a conventional tightening clamp or the like (not shown).

The Y-axis stage, in turn, supports an X-axis stage 62 slidably mounted, e.g., by rollers or bearings, on a support 61 for movement in a horizontal-plane X direction with respect to stage 58, on which the support 61 is rigidly mounted. The movement of the X-axis stage, indicated schematically by the double-line arrow 64, is under the control of an electromechanical motor (not shown). The same motor and measurement device described for the Y axis can be used here, typically allowing a total translation distance of about 20 cm. The motor, which is also referred to herein as an electromechanical device, is controlled by motion controller 76 in a control unit 79, as seen in FIG. 3A.

The X-axis stage supports a rotating chuck assembly 66 which includes a support block 67, housing a motor (not shown), and a chuck 68, secured to block 67 for rotation about the chuck's central axis 71. A mandrel 70, mounted on chuck 68, is positioned along axis 71 for rotation about axis 71. The mandrel, which is also referred to herein as a support element, is a conventional stent mandrel whose outer diameter is dimensioned to securely receive a stent, such as stent 72, for rotation with the mandrel. To this end, the circumference of the mandrel may be slightly tapered along its length to accommodate stents of different inner diameters and to allow a desired frictional fit of the stent on the mandrel.

Rotation of the mandrel, which is shown schematically by the double arrow 74, about its long axis (axis 71) is under the control of a motor (not shown). One exemplary motor is an ADRS-100-ES15472-A-X50 rotary servo motor available from Aerotech (Pittsburgh, Pa.), which integrates an encoder providing a resolution of 720,000 units per turn and provides unlimited rotation. As shown in FIG. 3A, the motor 73, which is also referred to herein as an electromechanical device, is controlled by motion controller 76 in control unit 79. As can be appreciated, during a coating operation, the mandrel rotation motor operates to rotate the mandrel and stent secured thereon at a selected rotational speed with respect to the fixed-position dispenser head, while the x-axis stage motor operates to move the mandrel in a linear direction along axis 71 with respect to the dispenser head. The combined rotational and linear motion is operable to move each skeletal element of the stent directly below the dispensing head, where coating can be applied to that skeletal element at a desired speed and position of the dispensing head with respect to that element.

As seen in FIG. 3A, the motion controller 76 is part of the control unit 79 that functions to convert speed and position signals from the system program to driving signals for the motors. In other words, the servo motors of the present invention may be computer controlled. The controller 76 may be capable of synchronizing the simultaneous motion of multiple motion axes, driving each servo motor according to the feedback of the associated motion encoder. One preferred motion controller is a CM3-AE-M0-H4, available from ACS Motion Control (Plymouth, Minn.).

The control unit further comprises a frame grabber 82 for the line camera 52. An example of such a frame grabber is the P3-PCI-CL13, available from BitFlow (Woburn, Mass.). This frame grabber can receive a position signal from the motion controller, allowing accurate image acquisition even during fast rotations of the stent. Another video frame grabber 80 converts video signals from the monitoring camera 56 to signals that can be processed or displayed by the workstation. The DFG/SV1 available from The Imaging Source LLC (Charlotte, N.C.), is an example of such a frame grabber, which provides three video signal inputs, allowing to alternatively display the image received from up to three monitoring cameras. Also shown are a keyboard 87 and mouse 83 for inputting coating specifications, such as the concentration of the drug in the coating solution, the total amount of drug desired in the coating, and other parameters that affect the deposition of the coating. Also included is a system monitor 85 for displaying user interfaces and video images before and during the coating operation, to allow some user control over the coating variables during operation.

Before considering software and algorithmic features of the apparatus for controlling motors during a coating operation, the setup and mechanical operation of the apparatus will now be briefly considered. Initially, a stent to be coated is placed on mandrel 70, which is already secured to the apparatus 30, and moved along the mandrel until it is securely anchored thereon. Alternatively, the stent may be secured to a mandrel, and the mandrel may then be mounted on the apparatus and tightened using a collet. The X-, Y-, and Z-axis stages are then adjusted so that one end of the stent is positioned in focus, below the line camera. At this point, with the mandrel rotating at a selected speed, line camera 52 images the stent, producing a 2-dimensional image of the stent that will be used for calculating coating paths, positions, and speeds, as considered in Sections C and D below. The X-, Y-, and Z-axis are then adjusted so that a chosen feature of the stent is positioned directly below the dispensing head, and a loaded syringe is mounted on the system.

Once the coating parameters are entered by the user or determined automatically, the dispensing of the coating solution, which may be varied through the coating operation or maintained relatively constant, and the motors are activated via motion controller 76 in the control unit 79. The outer elements of the stent are then coated with a desired amount of coating, with each element of the stent being coated as it moves beneath the dispensing head. This process is continued, through one or more passes, until the desired coating has been applied.

C. Method and Algorithms for Determining Traversal Paths

Figure 3B:
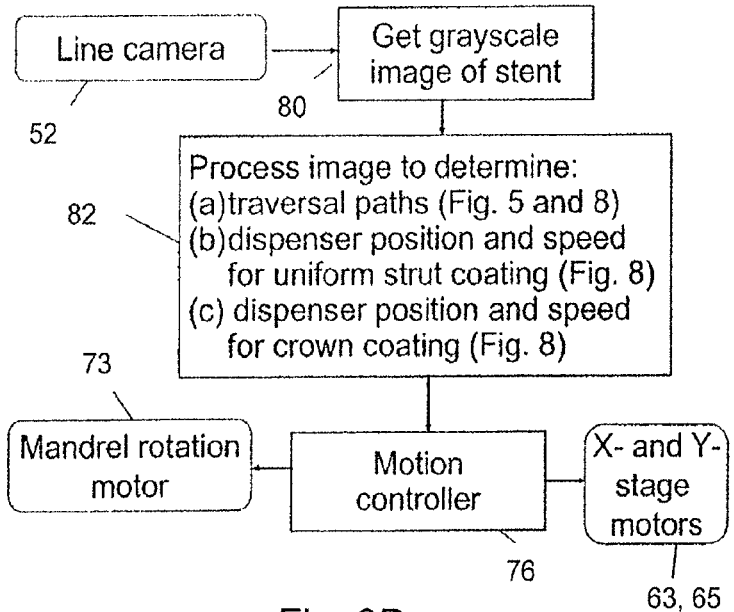

FIG. 3B illustrates the basic operations performed by the apparatus in converting a grayscale image of a stent into speed and position signals that will drive the appropriate coating operation motors. As shown, line camera 52 captures a grayscale image of the stent and this image is then processed via a series of software operations, indicated generally at 82 shown in FIG. 4, in order to (i) determine traversal paths by which the dispenser head is moved over the stent elements, described in this Section, (ii) determine variations of the position and speed of the dispensing head to optimize how the coating is deposited on the stent strut elements, described in Section D below, and (iii) determine dispensing speed, also described in Section D below.

Figure 4:
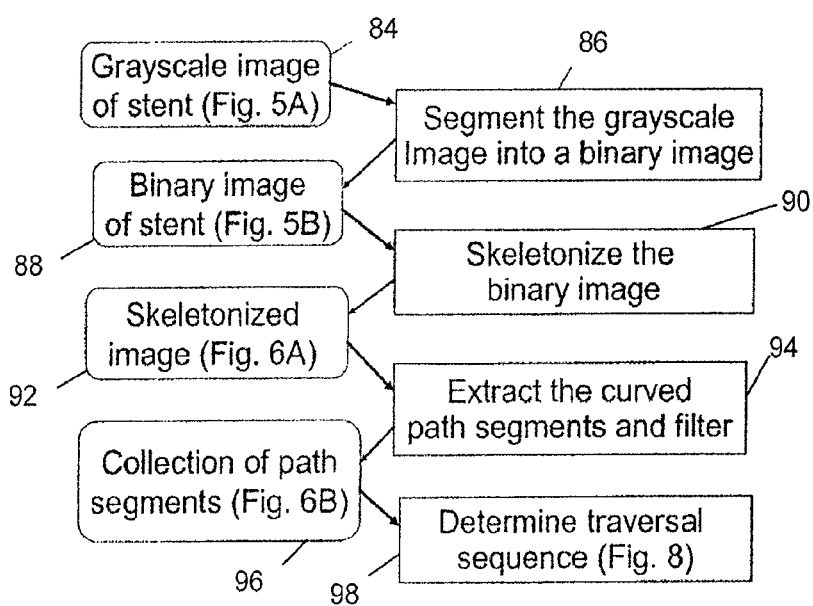
FIG. 4 is a flow diagram of steps for processing a grayscale image of a stent in determining a traversal path for the stent.

With reference to FIG. 4, the initial step of this process is to acquire a representation ("an image") 84 of the stent. This may be achieved by a variety of known means including, but not limited to, capturing a series of image tiles and assembling them together, and scanning the area where the stent is expected to be with an optical or a touch probe. The result of this process will be a 2-dimensional matrix containing signal information, which commonly can be represented as a grayscale image. The signal information can be luminosity or color information, a distance signal, or a light transmission signal. The axes of the matrix correspond, typically, to the longitudinal position along the stent, and the rotation angle of the stent.

In one embodiment, a light transmission system as described, for example, in U.S. Pat. No. 6,879,403 and U.S. Published Application No. 20070219615, may be used to obtain an image, whereby a line camera is aligned along the axis of the axially rotating stent fixture and focused at a distance adjusted to correspond to the radius of the stent. The mandrel may be a translucent rod, which diffuses the light emitted through it. The mandrel may be rotated around its axis for a full turn while a light transmission signal, obstructed where a strut is present, may be captured using the line camera. If the entire stent is not seen within one scan strip, the stent fixture is shifted axially, the rotation and scanning may be repeated as needed, and consecutive image strips may be assembled together.

Although the description here references a 2D representation of the stent, a 3D volumetric representation of the stent, acquired for example using a tomography technique, may also be used. The 2D image processing steps have known equivalents in 3D space, which could be applied to the extraction of path trajectory points as well. FIG. 5A shows a typical grayscale, 2-dimensional representation of a stent captured by the line camera in the apparatus, and fed through the image grabber into an image file in workstation 78. This grayscale image portion of the process is indicated at 84 in FIG. 4.

C1. Segmentation

Segmentation refers to the process of partitioning a digital image into multiple regions (sets of pixels), and simplifying the image into one that is easier to analyze. In addition, morphological noise removal and a histogram-based classification of pixels are image processing algorithms that may be part of the segmentation process. In one embodiment of the invention, only data points that are on or off the stent are considered as white and black image pixels, respectively. Any segmentation method or process known by those skilled in the art may also be used in accordance with the present invention.

In one embodiment of the invention, a morphological noise removal, utilizing an Opening transformation to remove small objects form the image or an Erosion technique to shrink these objects, may be applied to the image. A histogram-based method may be used to classify each pixel, based on its intensity value, as points that are on or off the stent (which may be represented by a binary value of 0 or 1 for each pixel). FIG. 4 shows the segmentation step 86 for converting a grayscale image 84 to a binary image 88. Illustrations of grayscale and binary images of a stent, in accordance with these image processing steps, are shown in FIGS. 5A and 5B, respectively.

Figure 6A:
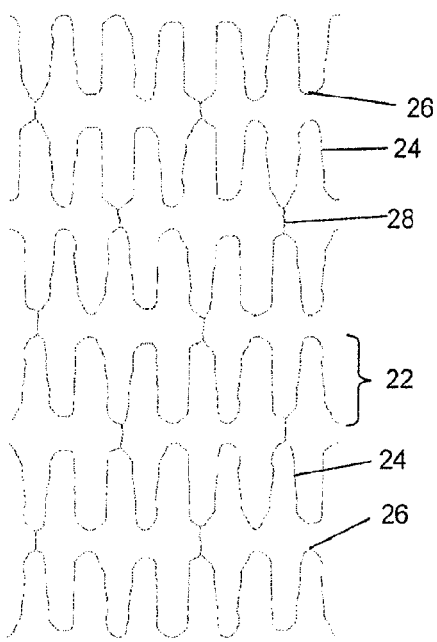
FIGS. 6A and 6B show a skeleton image of the same stent (6A), and a magnified portion of the same skeletal image rotated 90° (6B), respectively, where points A, B, and C in (6B) are intersection points, and 1 and 2 are two curved segments.

When capturing an image of a cylindrical object, such as the one represented in FIG. 1, and rotating it under a line camera, the resulting image may be represented as a flat image, such as the one illustrated in FIG. 5A. When considering the position of a point in the latter image, the vertical image coordinate may be represented as a coordinate along the axis of the cylindrical object. For example, the horizontal image coordinate may represent an angle of rotation. As a further example, at any coordinate x along the axis of the object, an image point at coordinate (x, 0°) is in effect identical to an image point at coordinate (x, 360°). Therefore, the right and left edges of the image represented in FIG. 5A, 5B, or 6A are actually adjacent to each other on the original cylindrical object.

This understanding should be taken into account when utilizing a morphological transform applied to neighboring image points (wherein image points are generally called "pixels"). With respect to FIG. 5A, corresponding pixels on the left and right edges of the image may be considered as adjacent to each other, as if the image was wrapping around and repeating itself.

C2. Skeletonization

Skeletonization, commonly called Medial Axes Transform, is a process by which a region of the image is reduced into a skeletal remnant that preserves the structure and connectivity of the original region. The region is thinned out until its medial elements, of a single pixel width, are exposed. The resulting image corresponds to what one would intuitively draw as the centerline of the strokes with which a region was drawn.

There are several known approaches to perform the skeletonization of an image. One example of such an approach utilizes an algorithm, which is disclosed in a document by David Eberly of Geometric Tools, LLC, entitled *Skeletonization of 2D Binary Images* (1988-2008). As shown in FIG. 4, during skeletonization, the stent region is iteratively eroded as long as it is more that 1 pixel wide.

In the present context, the skeleton image reflects the structure of the stent; in other words, it represents a collection of curve segments, which follow the centerline of the structural elements of the stent and intersect at junction points. A skeletonized binary image of the stent 92 is shown in FIG. 6A.

C3. Extraction of the Skeleton Image

In this step, shown at 94 in FIG. 4, the skeleton image is translated into a different in-memory representation that can more conveniently be used to define a traversal path. In the input image, continuous sequences of points (where each point has two neighbors) are extracted one by one, and converted into an in-memory sequence ("array") of point coordinate pairs. The output of this processing step will be a list of segments, which are called "Bones," each of which is defined by a single sequence of point coordinates that define the path, or trajectory, between two intersection points (defined as an image point that does not have two neighbors). Each end point of a "Bone" is called a "Joint." A list of Joints, which are defined by their coordinates, holds a reference to all Bones that end or start at that position.

Starting from an intersection point (a point on the skeleton image that has more than two neighbors), then searching adjacent image points for a neighbor that has not yet been visited, points are traversed one by one until another intersection point at the other end of the segment is reached. The coordinates of each point traversed, in order, are appended to the array of positions associated with a Bone. The position of each intersection point that has been traversed is included in the list of Joints.

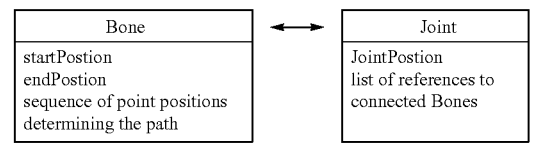

In computer science parlance, as is well known by those skilled in the art, the above Bones, referred to as edges or links or connections, and Joints, referred to as nodes or vertices, constitute a graph.

Figure 6B:
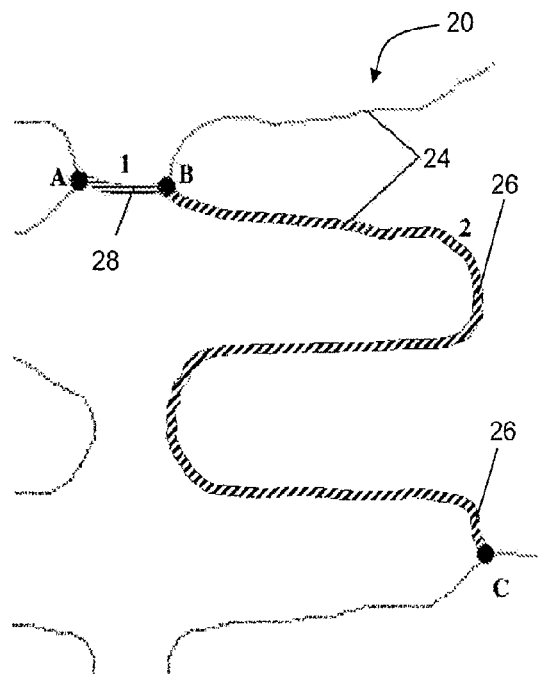
Figure 7:
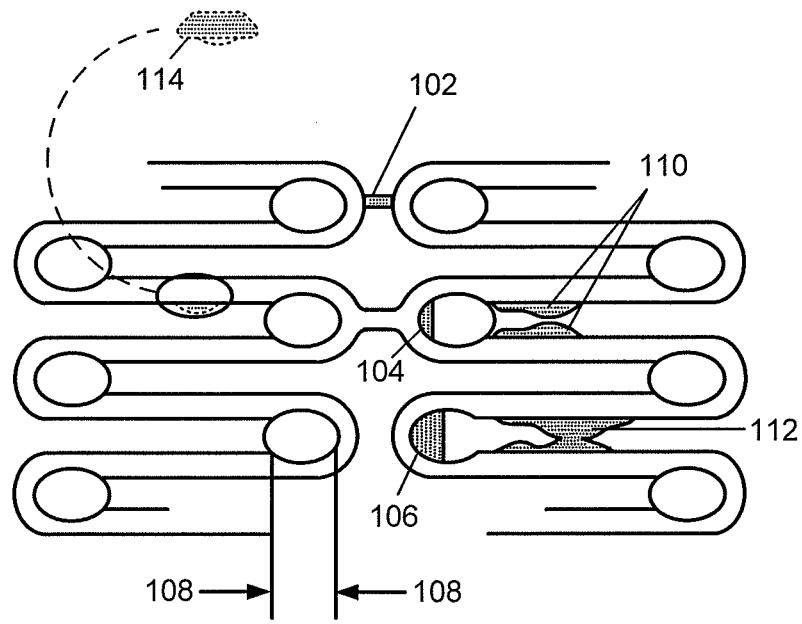
FIG. 7 illustrates various coating imperfections that can occur in coating a skeletal structure such as a stent.

FIG. 6B illustrates a magnified portion of the previous skeletonized image. A, B, and C are intersection points ("Joints") that have been identified, while 1 and 2 are two curve segments ("Bones") connecting Joints A and B and Joints B and C, respectively. The collection of path segments and Joints produced by the procedure is indicated at 96 in FIG. 4.

C4. Filtering the Bones and Joints Graph

One embodiment of the present invention comprises the following process, which may be performed iteratively, for filtering out one or more artifacts on the graph:

If a Joint is connected to a single Bone, it is suppressed, as well as the adjacent Bone.

A Joint that connects two Bones (which may be created by the previous step) is suppressed, and the two adjacent Bones are merged into a single Bone, juxtaposing their two point sequences into a single list.

Furthermore, Bones may be labeled or classified based on their properties, to facilitate or provide guidance, for further processing. For example, Bones may be labeled according to their length (as number of points). In some stent designs, short Bones correspond to links, and may be labeled as such. Other properties such as the horizontal (e.g., axial) or vertical (e.g., rotational) extent of the Bone may also be used to identify certain stent features. Alternatively, to facilitate later retrieval, Bones or Joints may be sorted according to their length, or to their location—for example, according to the leftmost coordinate in the sequence of positions associated with the Bone. In some cases, Bones identified by certain properties could also be suppressed (for example if some stent elements are not to be coated), or otherwise transformed, or be coated with a different number of passes. The labeling, classification and identification processes described above are not intended to be limiting of the invention but only exemplary.

C5. Generation of a Bone Traversal Sequence

The process of the present invention further comprises the determination of a traversal sequence for traversing the dispensing head over the stent elements, indicated at 98 in FIG. 4. Different traversal strategies may be implemented, and graph traversal strategies have been extensively studied. Two examples of exemplary approaches which have been implemented in existing embodiments of the invention include, but are not limited to, Single Traversal and Continuous Traversal Loop.

The Single Traversal approach comprises traversing each skeletal element only once. This approach includes, but is not limited to, the following:

1. Sort a list of Bones according to the leftmost coordinate that is visited.
2. Start the traversal from the first (leftmost) Bone in the list.
3. From the Joint at the end of the last visited Bone, look for an adjacent Bone that has not yet been visited:
   if a single non-visited Bone is found, continue the Bone traversal along that element and repeat this step.
   when more than one non-visited Bone is found, continue the traversal by selecting the Bone that is earliest in the list and is therefore more to the left.
   if all adjacent Bones have already been visited, select the leftmost Bone that has not yet been visited as the next one. A connecting motion to this Bone element, during which the dispensing will usually be interrupted, will be inserted in the Bone traversal sequence.

The Continuous Traversal Loop approach results in the generation of a continuous traversal loop, whereby the traversal starts and ends at the same Joint. This approach includes, but is not limited to, the following:

1. Identify and mark all the Bones that represent links of the stent (they can be identified as such by their shorter length).
2. Duplicate all the link elements in the list of Bones, adding these copies to the list of Bones.
3. Select any Bone element from which to start the traversal.
4. From the Joint that has been reached:
   if the previously traversed Bone was a non-link element, select an adjacent link element that has not yet been traversed.
   if the previously traversed Bone was a link element, select an adjacent non-link element that has not yet been traversed.

For the stent design illustrated in FIG. 5A or 56, the previous approach (duplicating the link elements) will transform the graph structure into an Eulerian circuit. An Eulerian circuit is a path in a graph which visits each edge exactly once and which starts and ends on the same vertex. With respect to the present invention, all Bones in the list (in which link elements have been duplicated) are traversed once, and the traversal ends at the same point where it was started. An advantage of this approach is that subsequent traversals of all the Bones can then be undertaken without interruption.

One aspect of this approach is that link elements are being traversed twice as often as the non-link (also called in-band) elements, possibly depositing excess coating over the links. To compensate for this, two possible approaches include, but are not limited to, the following:

(a) Double the motion speed when traversing link elements, relative to non-link elements. When keeping a constant dispensing rate, this will help balance the amount of coating deposited on the two types of elements.

(b) Insert in the traversal sequence additional traversals of non-link elements. For instance, the first time that a band of the stent is reached, an additional traversal of the non-link elements that constitute the band may be inserted in the sequence ("band extra turn").

C6. Traversal as a Sequence of Points

Once a sequence has been determined for traversing the Bones, a single sequence of positions can be generated. In order for each Bone to be traversed, the associated sequence of positions is copied, reversed if necessary with respect to the direction in which the Bone is traversed, and appended to a final list of positions. This final list of positions may store additional information with each point, such as the region of the stent on which it is located (e.g., link or Bone), and the current pass being performed. This final list of positions defines the base path along which the dispensing head is to traverse the stent.

Position information, as well as other parameters for each point, may further be processed or computed to modulate or affect parameters of the finally actuated motion.

D. Speed and Position Algorithms

---

Information available for every point along the path:
    Position
    Segment category
    Local curvature
    Local width of the strut
    Distance to adjacent segment ends
    Index of current layer
    Total number of layers
    Vector outside contour
Path motion actuation parameters:
    Motion Speed
    Dispensing rate
    Position (rotation and translation)
        Deviation from path
            "outer contour"
            "R-spread"
        Distance of dispensing head

---

This section discusses a variety of speed- and position-control algorithms that may be employed in a coating operation in accordance with one embodiment of the invention, in order to achieve a stent coating with desired characteristics, including, but not limited to, (i) a selected amount of total coating material applied, (ii) coating coverage of the entire outer surfaces of the stent elements and, optionally, spillover from the outer surfaces and over the side surfaces of the stent element, and (iii) reduction or elimination of coating imperfections of the type that can occur when a viscous coating solution is dispensed by micropipetting, as discussed in the Background of the Invention.

D1. Key Coating Parameters

The following parameters define the continuous motion of a dispensing needle along stent struts and are useful in understanding the operation of the coating apparatus under the control of the speed and position algorithms.

Motion Speed.

The motion speed defines the velocity at which the dispensing head moves along the path computed as described in detail above. In one embodiment of the invention, motion velocities of a few millimeters of strut length per minute, up to approximately more than 150 mm/min, were used. Speeds below 80 mm/min may contribute to spilling and webbing, because the deposition of the coating is increasingly driven by the liquid's surface tension forces. High motion speeds, above 150 mm/min, for example, increase the likelihood of a discontinuity in the deposition of the coating, as the liquid's surface tension is broken.

Once a coating path and average motion speed have been defined, the time required to perform the coating can be computed as the path length divided by the coating speed. For example, where the Path Length equals 300 mm and the Motion Speed equals 100 mm/min, the coating time is 3 minutes.

Dispensing Flow Rate.

The amount of coating that is desired on the stent and the concentration of the coating material in the coating solution determine the volume of coating solution to be deposited. Therefore, assuming a constant dispensing flow, the dispensing flow rate is also defined by the motion speed. For example, with respect to the previous example wherein the coating time equals 3 minutes, if 6 µl are to be dispensed, then, the flow rate will be 2 µl/min.

In one embodiment of the invention, the characteristics of the coating solution were determined during prior manual application of the coating. In view of the runniness and drying time of the solution, an optimal flow speed may be about 0.5 µl/min. Higher flows may lead to spilling and webbing of the coating, while lower flow values may be accompanied with the formation of strings. Various concentrations or dilutions of the coating formulation can be used. It should be noted, however, that the optimal value of the flow rate depends, in part, on the concentration of the coating formulation and also on the specific stent model being coated.

Number of Passes.

As described above, the dispensing flow rate and the motion speed are dependent on each other. To reduce the dispensing flow rate while preserving a chosen motion speed, the total path length can be altered by applying the coating in multiple passes. For example, by applying the coating in four passes, the total path length is conceptually multiplied by four, and the total coating time is multiplied by four as well. Thus, to dispense the same volume of coating formulation, the flow speed is divided by four as well.

To maintain uniformity of the coating thickness, motion speed, and dispensing flow, the number of passes can only be increased in discrete integer amounts. Therefore, the motion speed, the number of passes, and the concentration of the coating solution may need to be modified in parallel to obtain a desired dispensing rate.

D2. BandExtraTurn Balancing Coating Thickness Between Links and Bands

Ideally, the traversal path has few or no skips or discontinuities where the dispensing head is raised to a non-dispensing position, since skip motions are often accompanied with coating artifacts such as deposits or strings.

One solution to this problem is to determine paths that traverse every link twice, resulting in a pattern that can be traversed by an Eulerian loop path, where a pass starts and ends at the same point. To balance the doubled traversal of link paths, it is necessary to double motion speed over the stent links, so that links would then be coated twice as often but with half the dispensed volume corresponding to their length.

Another solution to this problem has been an approach referred to as BandExtraTurn. Instead of reducing the coating delivered over links during a pass, additional layers of coating can be applied over in-band struts. Within each band, a layer is added by performing a full turn of the rotary axis while remaining within the same band (an "extra turn"). Scattered over the longitudinal traversals of the stent normally performed during a single pass, the extra turns represent an alternative means of balancing the coating thickness between links and bands. Note that this additional turn also has the effect of increasing the total length of the path, and therefore the coating time and dispensing rate as well.

The table below summarizes the relationship between the Number of Passes (NoP) and BandExtraTurn values in the coating algorithms previously discussed.

| Number of coating layers deposited on Links | 2 * NoP |
| Number of coating layers deposited on Bands | BET + NoP |

It should also be noted that the Number of Passes and BandExtraTurn parameters may affect the processing previously described herein.

D3. R-Spread: Varying the Coating Trajectory Over Wider Struts

As noted above, it may be desirable to obtain a broader and more even coating over the struts and, in particular, across the wider portions of the struts. This can be achieved, when performing multiple passes, by deviating the trajectory of the dispensing head from the center of the strut and shifting it closer to either edge of the strut. This approach also helps achieve an overflow of the coating on the sides of the struts, which helps with adhesion of the coating and in distributing more of the coating to side surfaces of the stent. The parameters employed in this approach are named "R-Spread Margin" and "R-Spread Multiplier."

R-Spread Margin defines the maximum distance of the tracing path from the edge of the stent strut or crown (links may not be affected). Where the strut radius (i.e., half the strut width) exceeds this distance, the path may be modified to remain at this specified distance inward from the left or right edge, as measured along the R-axis. Where the calculated traversal path includes one or more extra band turns with each traversal, each layer deposited on the in-band strut will follow its own trajectory.

Within the multiple coating layers deposited on in-band struts, the path first follows one edge of the strut (e.g., upper edge), then the other edge of the strut (e.g., lower edge), and then converges linearly and symmetrically toward the central path during subsequent passes, as illustrated in FIGS. 9A and 9B. The third and subsequent passes may also be distributed more towards the center of the strut, or closer to the two initial edge passes, depending on the desired distribution of the coating (e.g., the amount of coating to be deposited on the strut edges). The trajectory determination involves a R-Spread Multiplier which is used to magnify the R-Spread displacement or margin from the original central path. For example, given a strut width of 100 µm, and an R-Spread Margin of 30 µm and a R-Spread Multiplier of 2.0, the path traced will be up to (100/2−30)*2.0=40 µm from the center line on the strut. R-spread functionality may be applicable to bands, since insufficient strut coverage is a problem that mainly affects the wider bands.

FIG. 9A illustrates the calculated trajectories over band element 116, each having struts 118 and crowns 120, and link element 122, located between bands 116. Four trajectories were determined using a R-spread margin of 30 microns, and a multiplier of 4, for four separate traversals, meaning three extra band turns in each band and a single path over the connecting links. The selected R-spread and multiplier values lead to four distinct paths over the greater-width struts and somewhat convergent paths over the narrower crowns, with all of the trajectories "contained within" the surface areas of the strut.

FIG. 9B illustrates the trajectories over the same portion of stent, but where a multiplier of 3 was used in combination with the 30 micron R-spread margin. The two outermost trajectories in the four paths carry the dispensing head outside the strut boundaries, and also lead to less path convergence within the crown elements. Thus, by increasing the R-spread margin multiplier in the calculation, the dispensing head can be brought closer to and then over the edges of the struts, for purposes of achieving greater spillover of dispensed material onto the side regions of the stent. More particularly, the R-spread margin and multiplier can be selected to produce a desired amount of spillover onto the side surfaces of the stent elements, thereby producing a stent having a selected ratio of coating material on its upper element surface versus its side surface.

In one embodiment of this invention, the trajectory deviation is applied only within bands of the stent, where larger struts are found in some coated stents. Alternatively, the deviation may also be applied by shifting the trajectory of the dispensing head only along the rotational (R) axis. Additional and alternative applications may also be used and the description herein is not meant to be limiting as will be readily appreciated by those skilled in the art.

In one preferred coating method, these parameters are selected to produce a coating in which the amount of coating material contained on the side surfaces is between about 50-100% of the amount of coating material on the stent's upper element surfaces. In one aspect, the invention includes a stent having both its upper and side surfaces covered with a coating, where the amount of coating material on the side surfaces is 50%-100% that of the coating on the stent upper surfaces.

D4. Needle Distance

The distance between the tip of the dispensing needle and the stent is an important factor affecting the deposition of the coating. The "needle elevation" coating parameter determines a needle elevation relative to the needle-stent contact point at which a position matching has initially been made.

Since the coating has been applied in multiple passes, because the deposited coating has a certain thickness, an additional "needle elevation increment" parameter may be used. This value, multiplied by the number of coating layers previously deposited on the currently coated strut, is added to the base needle elevation. Both elevation values are specified in micrometers (μm or microns). Typical needle elevation values are between 20 and 60 μm, and typical needle elevation increments are between 2 and 5 μm.

D5. Wider Contour, Faster Contour, Faster Thin Width

In some cases, it may be desirable to dispense less coating on specific strut features. For instance, to preserve the same coating thickness, less coating material should be deposited on a thinner strut than on a wider strut. Because it is preferred to keep a constant flow rate (as the fluid's viscosity and the elasticity of the dispensing system would impair the ability to vary it precisely), a preferred approach is to locally increase the motion speed.

Another path portion where a reduction of the dispensed coating amount may be desired is over stent crowns and wherever the strut follows a sharp turn. Webbing of the coating, as well as cracking during the expansion of the stent, tends to occur in those locations. Therefore, it may be desirable to associate an increase in the curvature of the strut to a local increase of the motion speed of the dispensing unit.

Another strategy which may reduce the appearance of webs on the inside of crowns involves allowing the dispensing unit to follow a path that remains on the outside of the strut. This has the tendency to pull the coating towards the outer edge of the strut curve by opposing surface tension forces that pull the dispensed solution towards the inside where webbing occurs.

The width of a strut is easily obtained from the image by measuring the distance from a path point to the closest stent edge. The curvature of a strut is defined as a "rectitude coefficient," as defined below. With reference to the crown and strut image shown in FIG. 10, sequential points A, B, C, D, E are positioned at fixed length intervals measured along the centerline of the strut. This length will be referred to as A. With regard to point D, which in this Figure is located within a crown, two neighboring points are selected along the base path at distance A preceding and following point D, which in this instance are illustrated as points C and E. The median of the segment delimited by these points is point M. The value KR(D) is the ratio of the direct distance of the two neighboring points (C,E) divided by their distance measured along the path (=2λ). KR is a rectitude coefficient, whose value varies from a maximum of 1, for a straight line, to a (theoretical) minimum of 0, if D was on a 180° turn between two straight segments. Also, vector o, which is the vector M→D, is defined as the "outer vector." This vector can be multiplied by a user-specified coefficient to determine a deviation of the trajectory of the dispensing head.

By applying the approach defined above to other points illustrated on FIG. 9, and other path points in-between, a rectitude coefficient and an "outer vector" can be obtained for every point along the path. The vector is nearly zero next to point B, and has an intermediate magnitude near point C. The dotted line diverging for the centerline illustrates a path obtained by deviating from the solid centerline trajectory by adding to the coordinate of each point its computed outer-vector multiplied by a coefficient of about 0.9. To provide further control and configurability, the outer vector coefficient can be separated into two components: one that applies to the horizontal image coordinate (motion along the X axis), and another that applies to the vertical coordinate (motion applied by the R axis). The ability to favor either component of the expanded motion is useful to separately affect curves with different orientations. The outer vector coefficient may also be independently specified for each pass, or be given a different value in different regions of the stent (e.g., links versus bands).

D6. Computing and Combining Speed Coefficients

A motion along an arbitrary path can be defined as a sequence of positions and the time interval between each pair of consecutive positions. For a fixed speed motion, each time interval is proportional to the distance of the two points. However, as described above, it is desirable for the motion speed to be changed locally, according to chosen parameters, to better control the deposition of the coating across various portions of the stent.

For example, assume that Tb is the base time interval for moving from a given point in the traversal sequence to the following one, with a constant speed. Tb is computed by dividing the distance to the following point (in millimeters), with a chosen arbitrary reference speed (e.g., 1 mm/s). Tb defines a reference traversal time for a constant-speed motion. If the speed over a given region of the stent is to be uniformly increased (over links, for example, as previously discussed), then the Tb coefficient can be multiplied in real time. For example, to double the motion speed over stent links, Tb may be divided by two.

As another example, assume Tt is defined as Tb multiplied by the strut width measured at a specified location (or a function of strut width, such as, for example, the square of the width value). If Tt is used as a traversal time to reach the next point, the resulting motion speed is thereby dependent on strut thickness. Now let Tc be Tb multiplied by a function of the Rectitude Coefficient. If Tc is used as a traversal time to reach the next point, the resulting motion speed is thereby dependent on the strut curvature (e.g., faster within turns).

Based on the foregoing, the point-to-point traversal times Tb, Tt, and Tc (and possibly other time values) may be combined to obtain an interpolated motion speed profile.

In one embodiment of the invention, the following two control values may be provided to the user for speed control: "faster contour" (Kc) and "faster thin width" (Kt). Each of those coefficients may be within an interval of 0 to 1, given as a percentage, and the total of those coefficients should not exceed 1. Each coefficient defines the influence of the corresponding time interval over the actual motion.

The actual time interval for traversing consecutive pairs of points along the path may be computed as follows:

$$T=k*(Tb*(1-Kt-Kc)+Tt*Kt+Tc*Kc)$$

The added coefficient k ensures that the total path traversal time corresponds to the requested average motion speed. This coefficient can easily be calculated using the pre-computed sum of the Tb, Tt and Tc time intervals as follows:

$$k=\text{desiredTotalTime}/(\text{sum}(Tb)*(1-Kt-Kc)+\text{sum}(Tt)*Kt+\text{sum}(Tc)*Kc)$$

where the desiredTotalTime is the path length divided by the desired average motion speed.

As a result of this approach, no quantitative units or magnitude is associated with the speed variation and "outer contour" coefficients. These coefficients may be optimized empirically through experimentation for any stent design.

D7. Early Start/Stop of Dispensing

In one embodiment of the invention, during dispensing through a simple needle, the coating solution is not instantly projected onto the strut. Instead, a drop suspended by the needle tip serves as an interface, or as a "buffer," between the source of the solution and the strut on which it is deposited. This drop contributes to spreading the solution over the strut surface, but also can interfere with the coating because of the complex physics of fluids, governed by surface tension, viscosity, drying times, and gravity.

Just prior to initiating the coating of a stent strut, a drop should ideally already be present at the needle tip. Therefore, the dispensing is usually activated 100 to 500 milliseconds before the motion along the coating path is initiated.

Figure 8:
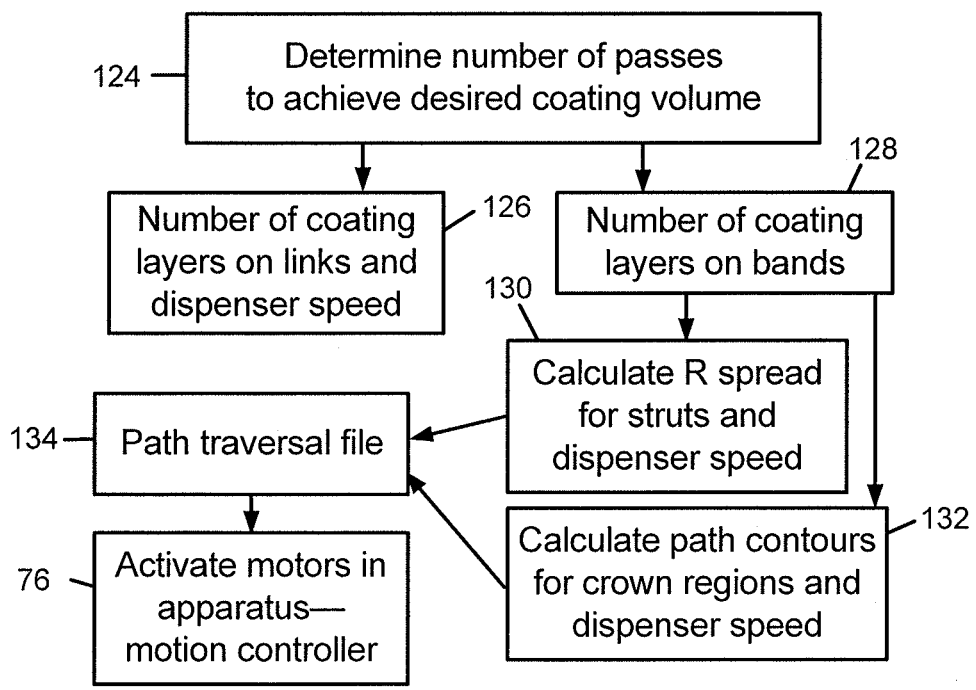
FIG. 8 is a flow diagram of the operation of the apparatus in determining traversal path speeds and dispenser positions.

The application of the above algorithms related to the relative speed and motion of the dispensing tip, as it moves along its traversal paths, can be appreciated from the block-flow diagram shown in FIG. 8. As illustrated in FIG. 8, the number of passes needed to achieve a desired coating amount and coverage 124, in accordance, for example, with the method described above, is determined. Next, the number of coating layers and dispensing head speed on the stent links 126 and/or the number of coating layers on the stent bands 128 is determined. Note that the number of coating layers on a band may be entered as input by the user, along with other input parameters like user Band Extra Turn.

The speed and position algorithms described above may be applied to determine optimal dispensing head positions and speed for the multiple passes over each band. As such, the R-spread for struts and the dispenser speed along the different path trajectories 130 and/or the path contours for crown regions and crown dispensing speeds 132 may be calculated, as detailed above. Once these traversal path variables are calculated, they are stored in a file 134 in, for example, the apparatus workstation. Upon initiation of a coating sequence, the files are input to the motion controller 76 (FIG. 3A), and used to drive the mandrel rotation and linear motion motors to achieve the desired predetermined position and dispenser speeds. Although not shown, the speed and position algorithms may also be used to calculate desired dispensing rate(s) and dispensing head elevation and elevation increments, under the control of separate servo motors.

Figure 11:
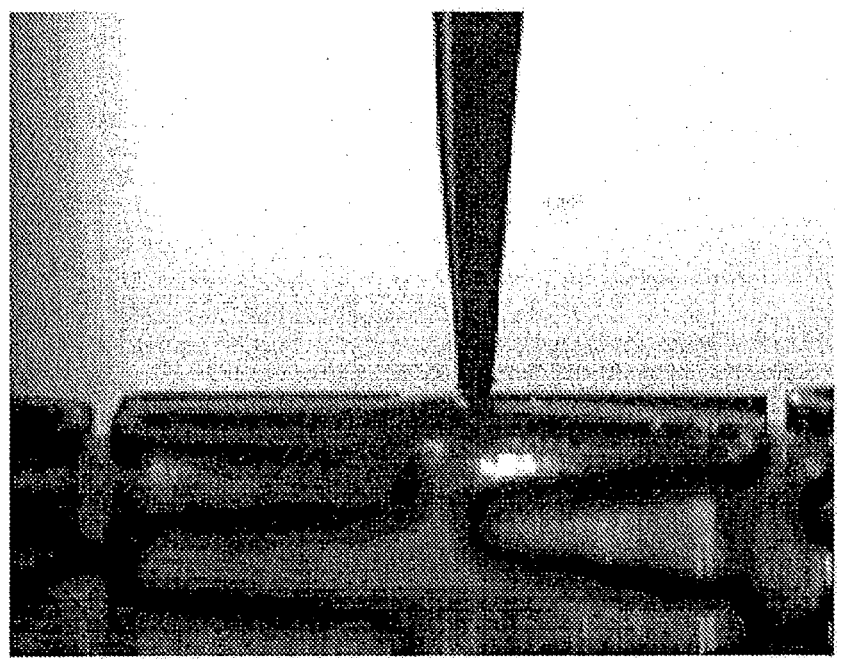
FIG. 11 is a display of an actual magnified video image, showing a dispensing tip over a stent in a coating operation in accordance with the invention.

Further, during a coating operation, the monitoring camera may be used for displaying a view of a portion of the stent receiving coating material and the tip of the dispensing head, thereby allowing the user to adjust tip elevation and/or dispensing rate to correct any coating imperfections that are observed. FIG. 11 shows a typical view presented to the user during a coating operation.

E. Sequence of Operation

The following describes one embodiment of the standard sequence of operations used to perform a coating process using the system of the present invention. It should be noted that variations to the sequence of operations may be made as known by those skilled in the art and, although not described herein, are also included within the scope of the claimed invention.

A user enters information about the stent being processed, including, for example, type, size, and amount of coating material to be applied.

A stent is then securely placed on the mandrel and a syringe is loaded with the coating material, e.g., liquid polymer solution such as, for example, a d-, l- or mixed d,l, polylactide (PLA) containing between 10-50% drug, such as rapamycin or another limus drug, such as "42-O-alkoxyalkyl limus drug, dissolved in a volatile solvent such as acetone. Examples of coating solutions that may be used are 50 µg of 42-O-(2-Ethoxyethyl) rapamycin (or 40-O-(2-Ethoxyethyl) rapamycin) and 50 µg of PLA per microliter of acetone; or 200 µg of drug per microliter of acetone (solution with no polymer). The loaded syringe is then attached to the dispensing device suspended by the Z-axis stage, as shown in FIG. 2, and the dispensing rod in the stage is lowered to a position of contact with the syringe plunger.

With the X-, Y- and Z-axis stages moved to position the line camera directly over the stent, the user initiates the scanning of the stent while the stent is rotated about the mandrel axis. The resulting image is displayed on the screen of the workstation. The user selects an identifiable point/feature on the image, and upon request from the user, the apparatus brings the dispensing unit over the stent. Because replacing the syringe or needle may have caused a displacement of the needle tip, the user verifies and eventually fine-tunes the positioning of the needle onto the feature chosen on the scanned image. The user then confirms that a precise positioning has been achieved.

When the user indicates that the coating sequence should start, the dispensing unit moves over the start point on the stent and at a specified distance. The user may then temporarily activate the dispensing unit until a drop of the coating solution appears at the tip of the needle. Upon final confirmation by the user, the coating process occurs automatically, and the user can monitor its progress on the monitoring camera(s), and observe if any artifact (webbing, bridging, etc.) is appearing. The motion of the stent is tracked and reflected on the view of the scanned stent image, allowing the user to verify that this view matches the position seen using the monitoring camera.

In case a failure is detected during the coating (e.g., limit switch encountered, inability to follow the planned coating path), an error alert may be displayed to notify the user of the problem. When the coating is completed, the user removes the stent from the system, and may repeat the above steps to coat subsequent stents.

From the foregoing, it will be seen how various objects and features of the invention are met. The apparatus is designed to process the image of a linked-element device, such as a stent, to determine traversal paths that are calculated, in terms of total number of paths, to optimize dispenser-head speed and minimize skips, for applying a selected amount of coating material to the stent.

In addition, various speed and position algorithms may be employed to ensure (i) coating coverage of the entire outer surfaces of the stent elements and optionally, through spillover from the outer surfaces, over side surfaces of the stent elements, and (ii) reduction or elimination of coating imperfections of the type that can occur when a viscous coating solution is dispensed by a needle or micropipette.

While the invention has been described in detail with reference to certain preferred embodiments thereof, it will be understood that modifications and variations are within the spirit and scope of that which is described and claimed.

What is claimed is:

1. An automated method of applying a coating on the outer surface of a stent whose tubular structure is composed of linked skeletal elements, comprising
    (a) processing an image of such a stent to determine (a1) paths along the stent skeletal elements by which a stent secured to a rotating support element that can be axially rotated and translated relative to a dispenser head that moves linearly relative to the support, along the support axis, such that some or all of the stent skeletal elements will be traversed, (a2) the relative speed of the dispensing head and support element as said paths are traversed, and (a3) positions of the dispenser head with respect to a centerline of the stent skeletal elements, as said paths are traversed, and
    (b) synchronously activating a first electromechanical device that controls the rotational speed of the support element and a second electromechanical device that controls the relative linear motion of the dispensing head with respect to the support element along the support element axis, in order to move the dispensing head relative to the support element along the paths and with the relative speeds and positions determined in step (a),
    wherein during step (b) the dispensing head dispenses a continuous liquid stream of coating material onto the stent skeletal elements, and wherein determining the relative speed of the dispensing head comprises determining speed coefficients between points that define the centerline according to varying features of the stent for controlling width of the continuous liquid stream as it is applied to the stent skeletal elements.

2. The method of claim 1, wherein step (a1) includes the steps of applying (i) a segmentation algorithm to determine the area occupied by the stent elements, a (ii) skeletonization algorithm, to determine the points of intersections of the stent skeletal elements, (iii) a path-traversal algorithm to determine the paths along the skeletal elements, and (iv) a speed and position algorithm to determine the speeds and positions of the dispenser head, relative to the support element, as it travels along said paths.

3. The method of claim 2, wherein applying said path-traversal algorithm is operable to determine paths by which the stent skeletal elements can be traversed by the dispenser head, in a selected number of passes over given portions of the skeletal element such that all the stent skeletal elements will be traversed at least once, and link and band elements of the stent may be traversed different numbers of times.

4. The method of claim 2, wherein said path-traversal algorithm is operable to determine the total length of the determined path and the volume to be dispensed, and said speed and position algorithms are determined so that the preselected amount of coating material is applied.

5. The method of claim 2, wherein the stent has substantially straight strut skeletal elements with widths greater than the width of the dispenser head, wherein said speed and position algorithm is operable to determine the positions of the dispensing head, relative to the width centerline of such straight strut skeletal elements, for different passes, such that coating is applied across the entire width of the straight strut skeletal elements in the course of several passes.

6. The method of claim 2, wherein said speed and position algorithm is operable to determine the positions of the dispensing head, relative to a width centerline of the stent elements such that, for different passes, the coating is applied across the entire width of the stent skeletal elements, creating coating material spillover onto the side surfaces of the stent skeletal elements in a desired amount between 50% and 100% of the amount of coating material applied to upper stent element surfaces of the stent skeletal elements.

7. The method of claim 2, wherein the stent has curved crown skeletal elements, wherein said speed and position algorithm is operable to determine the positions of the dispensing head relative to the width centerline of a crown element, and to control the speed of movement of the dispensing head, relative to the support elements, to minimize the potential for material-coat bridging between laterally-adjacent curved crown elements and meniscus formation across the inner edge region of a crown element.

8. The method of claim 2, wherein the stent has substantially straight strut skeletal elements connected by substantially rounded crown elements, wherein said speed and position algorithm is operable determine a dispenser-head speed that is dependent on the local curvature of the trajectory.

9. The method of claim 2, wherein the stent has connecting link elements, wherein said speed and position algorithm is operable to determine independent dispenser-head speeds for the link elements.

10. A computer-readable medium having instructions that are executable by a processor to carry out a method of applying a coating on the outer surface of a stent whose tubular structure is composed of linked skeletal elements, the method comprising
    (a) processing an image of such a stent to determine (a1) paths along the stent skeletal elements by which a stent secured to a rotating support element that can be axially rotated and translated relative to a dispenser head that moves linearly relative to the support, along the support axis, such that some or all of the stent skeletal elements will be traversed, (a2) the relative speed of the dispensing head and support element as said paths are traversed, and (a3) positions of the dispenser head with respect to a centerline of the skeletal stent elements, as said paths are traversed, and (b) synchronously activating a first electromechanical device that controls the rotational speed of the support element and a second electromechanical device that controls the relative linear motion of the dispensing head with respect to the support element along the support element axis, in order to move the dispensing head relative to the support element along the paths and with the relative speeds and positions determined in step (a), wherein during step (b) the dispensing head dispenses a continuous liquid stream of coating material onto the stent skeletal elements, and wherein determining the relative speed of the dispensing head comprises determining speed coefficients between points that define the centerline according to varying features of the stent for controlling width of the continuous liquid stream as it is applied to the stent skeletal elements.

11. The computer-readable medium of claim 10, wherein step (a1) includes the steps of applying (i) a segmentation algorithm to determine the area occupied by the stent elements, a (ii) skeletonization algorithm, to determine the points of intersections of the stent skeletal elements, (iii) a path-traversal algorithm to determine the paths along the skeletal elements, and (iv) a speed and position algorithm to determine the speeds and positions of the dispenser head, relative to the support element, as it travels along said paths.

12. The computer-readable medium of claim 11, wherein applying said path-traversal algorithm is operable to determine paths by which the stent skeletal elements can be traversed by the dispenser head, in a selected number of passes over given portions of the skeletal element such that all the stent skeletal elements will be traversed at least once, and link and band elements of the stent may be traversed different numbers of times.

13. The computer-readable medium of claim 11, wherein said path-traversal algorithm is operable to determine the total length of the determined path and the volume to be dispensed, and said speed and position algorithms are determined so that the preselected amount of coating material is applied.

14. The computer-readable medium of claim 11, wherein the stent has substantially straight strut skeletal elements with widths greater than the width of the dispenser head, wherein said speed and position algorithm is operable to determine the positions of the dispensing head, relative to the width centerline of such straight strut skeletal elements, different passes, such that coating is applied across the entire width of the straight strut skeletal elements in the course of several passes.

15. The computer-readable medium of claim 11, wherein said speed and position algorithm is operable to determine the positions of the dispensing head, relative to a width centerline of the stent elements such that, for different passes, the coating is applied across the entire width of the stent skeletal elements, creating coating material spillover onto the side surfaces of the stent skeletal elements in a desired amount between 50% and 100% of the amount of coating material applied to upper stent element surfaces of the stent skeletal elements.

16. The computer-readable medium of claim 11, wherein the stent has curved crown skeletal elements, wherein said speed and position algorithm is operable to determine the positions of the dispensing head relative to the width centerline of a crown element, and to control the speed of movement of the dispensing head, relative to the support elements, to minimize the potential for material-coat bridging between laterally-adjacent curved crown elements and meniscus formation across the inner edge region of a crown element.

17. The computer-readable medium of claim 11, wherein the stent has substantially straight strut skeletal elements connected by substantially rounded crown elements, wherein said speed and position algorithm is operable determine a dispenser-head speed that is dependent on the local curvature of the trajectory.

18. The computer-readable medium of claim 11, wherein the stent has connecting link elements, wherein said speed and position algorithm is operable to determine independent dispenser-head speeds for the link elements.

* * * * *